United States Patent
Yamazaki et al.

(10) Patent No.: US 7,431,050 B2
(45) Date of Patent: Oct. 7, 2008

(54) LIQUID DELIVERY DEVICE

(75) Inventors: Takeo Yamazaki, Yokohama (JP);
Atsunori Terasaki, Kawasaki (JP);
Takeshi Imamura, Chigasaki (JP);
Takahiro Ezaki, Yokohama (JP);
Susumu Yasuda, Tokyo (JP); Toru Nakakubo, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 523 days.

(21) Appl. No.: 10/537,231

(22) PCT Filed: Mar. 1, 2004

(86) PCT No.: PCT/JP2004/002499

§ 371 (c)(1),
(2), (4) Date: May 31, 2005

(87) PCT Pub. No.: WO2004/079241

PCT Pub. Date: Sep. 16, 2004

(65) Prior Publication Data

US 2006/0054226 A1  Mar. 16, 2006

(30) Foreign Application Priority Data

Mar. 3, 2003 (JP) ............ 2003-056141
Nov. 5, 2003 (JP) ............ 2003-375388
Feb. 26, 2004 (JP) ............ 2004-051277

(51) Int. Cl.
*F15C 1/04* (2006.01)

(52) U.S. Cl. ............ 137/827; 137/859; 137/517

(58) Field of Classification Search ........ 137/462, 137/460, 517, 859, 512.1, 512.15, 554, 475
See application file for complete search history.

(56) References Cited

U.S. PATENT DOCUMENTS

| | | | |
|---|---|---|---|
| 3,087,004 A | 4/1963 | Thorsheim | 136/86 |
| 5,171,137 A | 12/1992 | Todescat et al. | 417/571 |
| 5,225,852 A | 7/1993 | Uchida et al. | 346/134 |
| 5,274,399 A | 12/1993 | Uchida et al. | 346/134 |
| 5,291,256 A | 3/1994 | Kitajima et al. | 355/290 |
| 5,293,898 A | 3/1994 | Masloff | 137/517 |
| 5,351,112 A | 9/1994 | Naito et al. | 355/233 |
| 5,563,698 A | 10/1996 | Okada | 355/309 |
| 5,579,083 A | 11/1996 | Naito et al. | 355/50 |

(Continued)

FOREIGN PATENT DOCUMENTS

GB  700449  12/1953

(Continued)

*Primary Examiner*—John Rivell
*Assistant Examiner*—Cloud K Lee
(74) *Attorney, Agent, or Firm*—Fitzpatrick, Cella, Harper & Scinto

(57) ABSTRACT

A fluid delivery device is provided which comprises a microchannel device for cutting out a certain amount of a sample from a micorochannel by controlling a valve opening. The fluid delivery device has a valve for controlling a flow of a fluid, comprising a flow channel for the fluid, and a valve in the flow channel, wherein the valve operates in accordance with a pressure difference between the upstream side and downstream side of the valve caused by the flow of the fluid through the flow channel, allowing the fluid to flow when the pressure difference is lower than a prescribed value $P_0$, and intercepting the fluid not to flow when the pressure difference is $P_0$ or more.

7 Claims, 16 Drawing Sheets

U.S. PATENT DOCUMENTS

| | | | | |
|---|---|---|---|---|
| 5,694,977 | A * | 12/1997 | Clark | 137/467 |
| 5,761,600 | A | 6/1998 | Murata | 399/403 |
| 5,800,690 | A * | 9/1998 | Chow et al. | 204/451 |
| 5,819,151 | A | 10/1998 | Naito et al. | 399/367 |
| 5,900,130 | A | 5/1999 | Benvegnu et al. | 204/453 |
| 5,915,159 | A | 6/1999 | Okada | 399/371 |
| 5,960,821 | A * | 10/1999 | Johnson | 137/460 |
| 6,120,020 | A | 9/2000 | Asao | 271/189 |
| 6,142,461 | A | 11/2000 | Asao et al. | 270/58.09 |
| 6,153,073 | A | 11/2000 | Dubrow et al. | 204/453 |
| 6,182,941 | B1 * | 2/2001 | Scheurenbrand et al. | 251/129.04 |
| 6,219,503 | B1 | 4/2001 | Miyake et al. | 399/85 |
| 6,220,592 | B1 | 4/2001 | Watanabe et al. | 271/241 |
| 6,290,220 | B1 | 9/2001 | Takehara et al. | 270/58.12 |
| 6,330,422 | B1 | 12/2001 | Sato et al. | 399/382 |
| 6,353,726 | B1 | 3/2002 | Murata et al. | 399/407 |
| 6,371,472 | B1 | 4/2002 | Miyake et al. | 270/58.14 |
| 6,386,080 | B1 | 5/2002 | Okamoto et al. | 83/73 |
| 6,398,203 | B1 | 6/2002 | Saito et al. | 270/58.12 |
| 6,398,214 | B1 | 6/2002 | Moteki et al. | 271/220 |
| 6,443,180 | B1 * | 9/2002 | Samuelson et al. | 137/460 |
| 6,450,934 | B1 | 9/2002 | Coombs | 493/383 |
| 6,471,429 | B1 | 10/2002 | Isobe et al. | 400/582 |
| 6,601,840 | B2 | 8/2003 | Boss et al. | 270/58.08 |
| 6,603,951 | B2 | 8/2003 | Sato et al. | 399/382 |
| 2002/0129690 | A1 | 9/2002 | Yaginuma et al. | 83/628 |
| 2002/0163119 | A1 | 11/2002 | Kawata | 271/207 |
| 2003/0049063 | A1 | 3/2003 | Suzuki et al. | 399/407 |
| 2004/0123898 | A1 * | 7/2004 | Yamashita et al. | 137/7 |
| 2004/0231726 | A1 * | 11/2004 | Nakajima et al. | 137/505.18 |
| 2005/0154345 | A1 * | 7/2005 | Milleker et al. | 137/554 |
| 2006/0021651 | A1 | 2/2006 | Sugioka et al. | 137/112 |

FOREIGN PATENT DOCUMENTS

| | | |
|---|---|---|
| JP | 04-252879 | 9/1992 |
| JP | 06-066769 | 3/1994 |
| JP | 10-292873 | 11/1998 |
| JP | 2001-070453 | 3/2001 |
| JP | 2002/355798 | 12/2002 |
| WO | WO 01/78893 | 10/2001 |

* cited by examiner

LIQUID DELIVERY DEVICE

TECHNICAL FIELD

The present invention relates to a liquid delivery device having a valve for controlling a flow of a fluid, particularly to a liquid delivery device having a valve for controlling a flow of a fluid for use in a miniaturized analysis system (µ-TAS: micro total analysis system) for conducting chemical analysis or chemical synthesis on a chip.

BACKGROUND ART

In recent years, with development of microfabrication techniques, the systems are attracting attention which comprise microchannel, microfluidic devises such as a pump, and a valve, and a sensor integrated on a substrate like glass or silicon or polymer, and conduct chemical analysis on the substrate. Such a system is called a µ-TAS (micro total analysis system), or lab-on-a-chip. The miniaturization of the chemical analysis system decreases an ineffective space volume and remarkably decreases the sample amount. The miniaturization enables also shortening of the analysis time and decrease of power consumption of the entire system. The miniaturization is promising for lowering the price of the system. Further, the µ-TAS is promising in medical services such as home medial care and bed-side monitoring, and biotechnologies such as DNA analysis and proteome analysis.

For the µ-TAS, various types of valves have been disclosed for controlling the fluid flow in a microchannel. For instance, a microvalve formed on a silicon substrate by micro-machining is disclosed by M. Esashi, S. Shoji, and A. Nakano: "Normally closed microvalve and micropump fabricated on a silicon wafer", Sensors and Actuators, Vol.20, No.1-2, pp. 163-169, 1989. This valve is capable of controlling a fluid flow by driving a diaphragm by a piezoelectric actuator. This document discloses also a one-way valve supporting a driving member elastically on a polycrystalline silicon plate. This one-way valve actuates a movable part by action of the flowing fluid itself to close a hole formed in opposition to the driving mechanism to intercept the flow channel. Such a valve which is driven by the fluid itself without an actuator is called a passive valve. The passive valve employing no actuator is capable of controlling the fluid with a simple structure of low production cost advantageously.

For the µ-TAS, various types of flowsensors been disclosed for controlling a flow of fluid in a microchannel. Japanese Patent Application Laid-Open No. 2002-355798 discloses a process for computing a flow rate, with a heater formed from an electroconductive thin film and a temperature sensor in a flow channel, by detecting the temperature change corresponding to the flow rate by change of resistivity of the electroconductive thin film. Such a flowsensor can be incorporated in a microchannel for measuring a flow rate in a microchannel.

On the other hand, many examples have been reported on utilization of electroosmotic flow for cutting out a certain amount of a sample from a microchannel. In the electroosmotic flow method, a voltage is applied between liquid delivery points to produce a driving force in the entire liquid. This method is suitable especially for delivering microchannel of 100 µm or finer. By utilizing this phenomenon, a sample-cutting system is often employed. For example, in a liquid delivery device 800 shown in FIG. 8A, a liquid is allowed to flow by electroosmosis from reservoir 802 through flow channel 806, intersection 809, and flow channel 808 to reservoir 804; and then as shown in FIG. 8B, the liquid is allowed to flow from reservoir 801 through flow channel 805, intersection 809, and flow channel 807 to reservoir 803 to cut out the liquid in the portion of intersection 809 to take a certain amount of sample 810. This sample is delivered to an analysis section. Hereinafter, the certain amount of cut-out sample is defined as a "sample plug". Nowadays various improvements are being made in shape control of the sample plug, delivery flow channel, and efficiency of the system, and so forth.

U.S. Pat. No. 5,900,130 discloses time control of the potential between the electrodes for retardation of spread of a sample in the intercrossing flow channel in liquid introduction and for control of the amount and shape of the sample plug at its formation by.

U.S. Pat. No. 6,153,073 discloses sophistication of combination of the flow channels to introduce two kinds of fluids cyclically into one and the same analysis section.

In the aforementioned prior art techniques utilizing the electroosmosis, the components of the solute in the sample plug delivered by the electroosmosis are different in migration rate depending on the mass and electric charge thereof. Consequently, the components in the sample plug are separated according to the difference in the migration rate, for example as shown by the numeral 811 in FIG. 8C. The components contained in the solution can be analyzed by outside detector 812. In other words, in this system, the separation of the components begins immediately after formation of the sample plug, and the movement of the sample plug thereafter is not a simple delivery process, but is a part of the analysis, the system being integration of sample delivery and the sample analysis.

DISCLOSURE OF THE INVENTION

Conversely, however, the immediate beginning of the component separation after sample plug formation makes it impossible to retain the original composition of the sample during the delivery. Therefore, the above process cannot be utilized in the case where the electrophoretic separation is undesirable, for instance, in the case where a certain amount of the sample is delivered to outside analysis apparatus. Further, the electroosmosis generates a low driving pressure, being not suitable for introduction of the sample to an analysis apparatus having a high flow resistance such as an HPLC column.

In another method, a fluid is delivered by application of a pressure by a pump or the like and the flow channel is controlled by a microvalve to cut out a certain amount of a sample. However, known microvalves require an external power source such as a piezoelectric element, electrostatic driving means, and a pressure source, and complicated structure of the device. Conventional passive valves, although simple in the structure, can serve only as a one-way valve or a check valve. Therefore, a sophisticated system such as the one for delivering a certain amount of a sample cannot be constituted by using conventional passive valves only.

The present invention intends to provide a passive valve for constituting a complex system, for instance, to deliver a certain amount of a sample. Further the present invention intends to provide a fluid delivery device comprising a microchannel controlled by opening of a valve for cutting out a certain amount of the sample from the microchannel.

In a process of measuring a liquid flow rate with a conventional flowsensor and adjusting a liquid delivery pressure and opening of a valve corresponding to the flow rate, both a flowsensor and a microvalve capable of active driving are necessary. The conventional flowsensor and the active-driven microvalve are complicated in the structure, so that the provision of both the flowsensor and the microvalve will make larger the entire system disadvantageously.

The present invention intends also to provide a fluid delivery device comprising a passive valve having a simple structure and serving also as a flowsensor.

The present invention provides a fluid delivery device having a valve for controlling a flow of a fluid, comprising a flow channel for the fluid, and a valve in the flow channel, wherein the valve operates in accordance with a pressure difference caused by the flow of the fluid through the flow channel between the upstream side and downstream side of the valve, allowing the fluid to flow when the pressure difference is lower than a prescribed pressure $P_0$, and intercepting the fluid flow when the pressure difference is $P_0$ or more.

The present invention provides also a fuel cell having a fuel storing section for storing a fuel, a power generating section for generating electric power by use of the fuel, and a valve provided between the fuel storing section and the power generating section, wherein the valve operates in accordance with a pressure difference between the upstream side and downstream side of the valve caused by flow of the fluid through the flow channel, allowing the fluid to flow when the pressure difference is lower than a prescribed pressure $P_0$, and intercepting the flow of the fluid when the pressure difference is $P_0$ or more.

The fluid delivery device of the present invention employs a valve which is controlled for opening and closing by changing the pressure of the fluid flowing through a flow channel, as a method for cutting out a certain amount of a sample from a microchannel. Therefore, components of the fluid can be delivered to an outside analysis apparatus by keeping the original composition without separation of the fluid components during the delivery. A high pressure is applied for the sample delivery. Therefore, this device is useful particularly as the fluid delivery device employing a valve for controlling a flow of a fluid for use in a miniaturized analysis system (μ-TAS) for conducting chemical analysis or chemical synthesis on a chip.

A method for introducing a sample into an analyzing device connected with the outside of the liquid delivery device mainly is explained in the following. A usage of the present invention with the method has an advantage in that a plurality of analyzing devices can be used by replacing the connected analyzing device with another analyzing device to be connected. The present invention is, however, limited to this usage. Alternatively, both a region on which the liquid delivery device of the present invention is located and a region having the analyzing function may be formed on a common TAS chip. This embodiment can reduce the delivery time since the analyzing region is formed in the vicinity of the delivery device. In addition, any connecting portion is unnecessary for the embodiment so that the sample plug hardly loses the shape, to improve the reliability of analysis. Further, the dead volume can be decreased, which enables small amounts of the buffer solution and the mobile phase.

The fluid delivery device of the present invention can serve also as a switch or a flowsensor, realizing a microchannel system for delivery of a fluid by controlling the flow rate with a simple structure of the device. In particular, the fluid delivery device of the present invention is useful in a miniature fuel cell which requires a simple structure of the cell and precise control of the fuel feed.

BEST MODE FOR CARRYING OUT THE INVENTION

The embodiments of the present invention are explained below in detail.

(Valve)

Figure 3A:
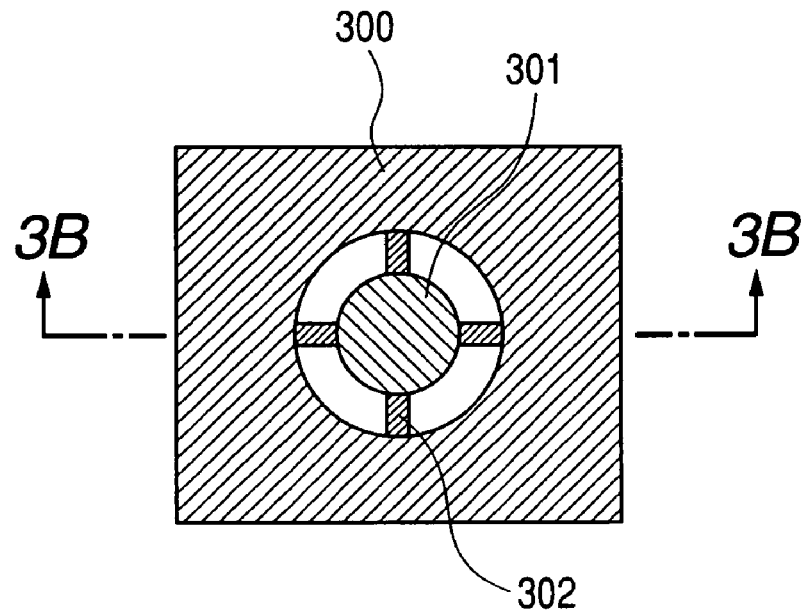
FIGS. 3A and 3B are schematic drawings showing an embodiment of a liquid-controlling element driven by a pressure difference caused by flow of a liquid.
Figure 3B:
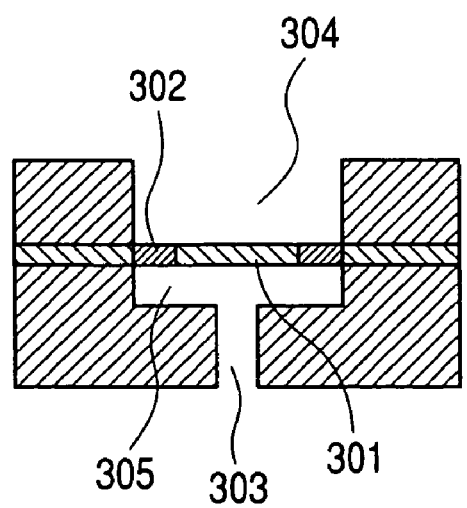

FIGS. 3A and 3B show schematically an example of the structure of the valve of the present invention. FIG. 3A is a plan view, and FIG. 3B is a sectional view, respectively of valve 300 of the present invention. The channel in the valve is constituted of a region of a small channel 303 and a region of large channels 304, 305. The intercepting part is a flat plate 301. This flat plate 301 is supported elastically by spring 302 between channels 304 and 305 to be perpendicular to the channel at a certain distance from inlet of channel 303. The diameter of flat plate 301 is larger than the diameter of channel 303, whereby flat plate 301 will intercept the flow of the fluid when flat plate 301 is displaced toward channel 303 to reach the boundary between channel 303 and channel 305.

Figure 4A:
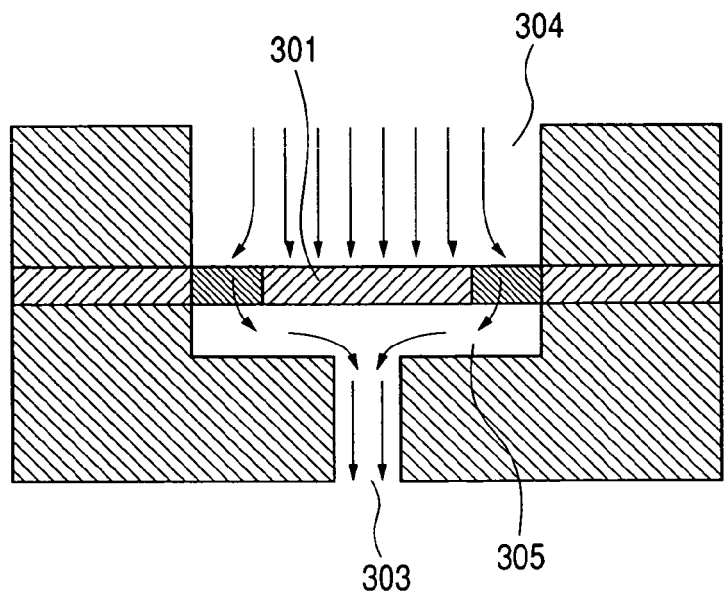
FIGS. 4A, 4B and 4C are schematic drawings showing another embodiment of a liquid-controlling element driven by a pressure difference caused by flow of a liquid.

FIG. 4A shows flow of the liquid from channel 304 to channel 303 in this valve. Such a liquid flow causes pressure drop by flowing through channel 305, causing a pressure difference between the surface of flat plate 301 at the side of channel 304 and the surface thereof at the side of channel 305. This pressure difference drives flat plate 301 toward the inlet of channel 303.

Figure 4B:
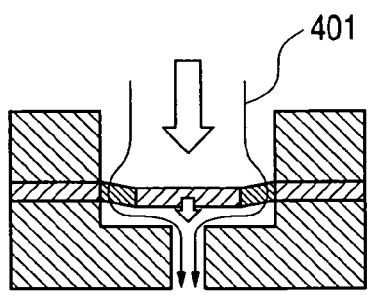

FIG. 4B shows the state of the valve when pressure difference $P_1$ caused by the liquid flow from channel 304 to channel 303 is smaller than threshold value $P_0$. Flat plate 301 is displaced by the pressure difference between the side of channel 304 and the side of channel 305, but will not come to close the inlet of channel 303 owing to the restoring force of spring 302 holding the flat plate. Therefore the fluid flows from channel 304 to channel 303 as shown by arrow 401. On stopping the delivery of the liquid, flat plate 301 returns to the original position by the righting moment of spring 302.

Figure 4C:
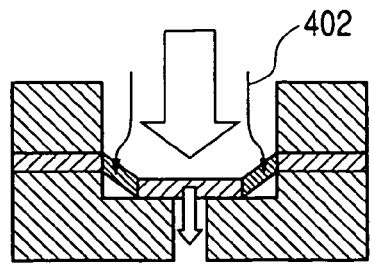

FIG. 4C shows the state of the valve when pressure difference $P_2$ caused by the liquid flow from channel 304 to channel 303 is larger than threshold value $P_0$. Flat plate 301 is displaced by the pressure difference between the side of channel 304 and the side of channel 305 to close the inlet of channel 303. Thereby, the flow of the fluid is stopped as shown by arrow 402 at channel 304, and flat plate 301 is kept sealing the inlet of channel 303 by the pressure of the liquid. On removing the pressure from the side of the channel 304, flat plate 301 comes apart from the inlet of channel 303 by righting moment of spring 302 to return to the original position.

From the constitution of this valve, it is clear that the flow from channel 303 to channel 304 is not intercepted invariably. Therefore, this valve can also serve as a check valve when used at a pressure difference caused by the flow from channel 303 to channel 304 larger than threshold value $P_0$.

A liquid delivery mechanism, which causes pressure difference caused by a flow of a liquid at the valve, enables constitution of a system for controlling a flow of a fluid by controlling the opening and closing of a valve.

The pressure range for driving the valve depends on a spring constant of spring 302, the distance between flat plate 301 and channel 303, the diameter of the flat plate 301 and the flow channel 303. The spring constant of spring 302 is a function of the spring length, spring thickness, numbers of the spring, and the spring material. A valve which opens or closes within a required pressure range can be designed by optimizing the above factors. In a closed state of the valve, flat plate 301 is held by the pressure of the fluid to give a high sealing effect with a high strength.

On stopping the fluid delivery, flat plate 301 returns to the original position by the righting moment of the spring. Therefore, the phenomenon of sticking, namely adherence of the flat plate onto the opposing substrate by surface tension without returning to original position, is less liable to occur. Such sticking is often a problem in conventional microvalves.

In the case where the above sticking causes no problem, the spring constant may be lower. Thereby the valve can be designed to keep a closed state without returning flat plate 301 to the original position by surface tension after stop of the fluid delivery. In such a valve, flat plate 301 can be returned to the original position by application of a pressure from the side of channel 303. The same effect can be obtained by shortening the distance between flat plate 301 and channel 303, and decreasing the righting moment of the spring in the closed state.

Spring 302 and flat plate 301 is preferably made from a material which is resistant to the solution subjected to the analysis and is resistant to some extent to elastic deformation, the material being exemplified by silicon. A resin like silicone may be used therefor. The surface thereof may be coated. The material of the substrate for forming the channel is not limited insofar as it is resistant to the analysis solution, the material including glass, silicon, and silicone resins. For employing electroosmotic flow, a material for producing electroosmotic flow may be used.

By using an intercepting part in a flat plate shape with a gap from the opposing substrate, the fluid pressure drops by passage of a fluid through the gap to cause pressure difference between the both sides of the intercepting part. This pressure difference moves the intercepting part toward the substrate.

The shape of the intercepting part is not limited provided that it is capable of closing the opposing aperture. A circular shape is preferred in view of symmetry of the flow. In particular, to a channel having a circular cross section, a circular flat plate is preferably placed with its center to coincide to that of the channel. Thereby the flow of the fluid and the pressure distribution in channel 305 are made symmetrical to the center axis to stabilize the displacement of the intercepting part.

The valve of the present invention shown in FIGS. 3A and 3B has flat plate 301 supported by springs 302. In such a valve, flat plate 301 can be displaced by deformation of the spring only without deformation of the flat plate, where the displacement of flat plate 301 is stable, to obtain a stable threshold pressure. It is necessary for deforming only spring 302 to design the spring with a small spring constant. Small thickness and small length in each spring 302 enables the spring constant of the spring to be small. A reduction of the number of springs is also effective in reducing a spring constant of all of the springs. It is also effective in obtaining a shape having little deformation to design flat plate 301 to have a relatively great thickness.

It is also possible to obtain flat plate 301 and spring 302 both of which are deformed by designing flat plate 301 with a small thickness and spring 302 with a considerable spring constant. In the case where both the flat plate and the spring are deformed, the center of flat plate 301 is deformed into a concave shape, whereby it is possible to close channel 303 along the outermost portion. As a result, the improvement of sealing property can be therefore expected.

The shape of the cross-section of spring 302 is not specially limited. The spring may be in a shape of a plate having a rectangular cross-section as shown in FIGS. 3A and 3B, or in a curved shape or a zigzag shape. The thickness of the spring may be different from that of the flat plate portion.

When a circular flat plate is supported with the center to coincide with the center of a channel in a channel having circular cross-section, the supporting positions by springs 302 is preferably symmetrical to the center axis. Thereby the pressure distribution in channel 305 is made symmetrical to the center axis, and the displacement of the flat plate is also made symmetrical thereto, giving a stable threshold pressure, and improving the sealing efficiency in the closed state.

In supporting the flat plate with plural springs, the spring constants of the respective springs are preferably made equal in view of the stability of displacement of the flat plate.

In the example of the above description, the intercepting portion is supported elastically by flat springs. However, the embodiment of the present invention is not limited thereto. For instance, the intercepting part may be supported elastically at one end by a cantilever, or at both ends by a beam.

(Bypass Line)

A fluid delivery system employing a valve of the present invention is explained below.

Figure 9:
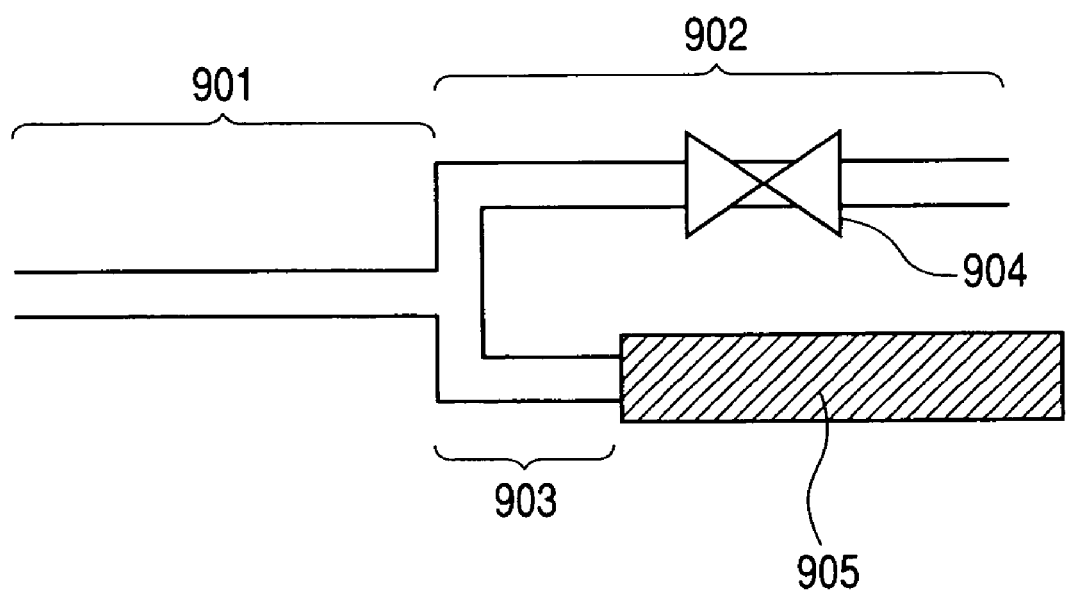
FIG. 9 is a schematic drawing showing an embodiment of a method of the present invention for delivering a liquid.

FIG. 9 illustrates a fluid delivery system employing a valve of the present invention. This system is constituted of flow channel 901, bypass flow channel 902, flow channel 903, valve 904, and HPLC column 905. The flow channel 901 is branched at the downstream end portion thereof into bypass flow channel 902 and flow channel 903. Flow channel 903 is connected to HPLC column 905. Valve 904 is provided in bypass flow channel 902. This valve 904 has a constitution similar to that of the above-explained valve. In FIG. 9, a flow from left to right is allowed to pass when the pressure difference between the both faces of the valve is smaller than $P_0$, and the flow is intercepted when the pressure difference is not smaller than $P_0$.

In HPLC analysis, the sample is sometimes pre-treated for washing, concentration, or the like in pretreatment portion at the upstream portion of the column. In the system shown in FIG. 9, a sample having been treated at a pre-treating section (not shown in the drawing) at the upstream side of flow channel 901 is introduced through flow channel 901 and flow channel 903 to HPLC column 905. If an initial portion of the sample introduced from the pre-treating section to flow channel 901 contains much contaminant and is not suitable for the analysis, the initial contaminated portion of the sample is introduced to bypass flow channel 902 not to deliver it to column 905 to enable accurate analysis.

In delivering a sample from the pre-treatment section to flow channel 901, the sample is delivered initially under conditions (introduction pressure, introduction flow rate) to keep the pressure difference between the both faces of valve 904 to lower than threshold $P_0$. In this delivery state, valve 904 is kept open. The flow resistance at the side of flow channel 903 and HPLC column 905 is much greater than flow resistance of bypass flow channel 902. Therefore, the sample which may contain a contaminant is delivered to the side of bypass flow channel 902, not delivered to HPLC column 905.

After lapse of a sufficient time, the sample is delivered under the conditions (introduction pressure, introduction flow rate) to obtain the pressure difference of threshold $P_0$ or higher between the both faces of valve 904. Thereby, valve 904 comes to be closed, and the sample is delivered through flow channel 903 to HLPC column 905.

As explained above, valve 904 of the present invention is provided in bypass line 902 to control the liquid delivery conditions. Thereby, a portion of the sample delivered from the pre-treatment section but not suitable for the analysis can be introduced to bypass line 902.

In the above explanation, an HPLC column is taken as an example. The scope of the present invention is not limited thereto. A system similar to the one of this embodiment is applicable in any fluid element requiring a bypass line.

(Introduction of a Certain Amount of Sample)

Figure 1A:
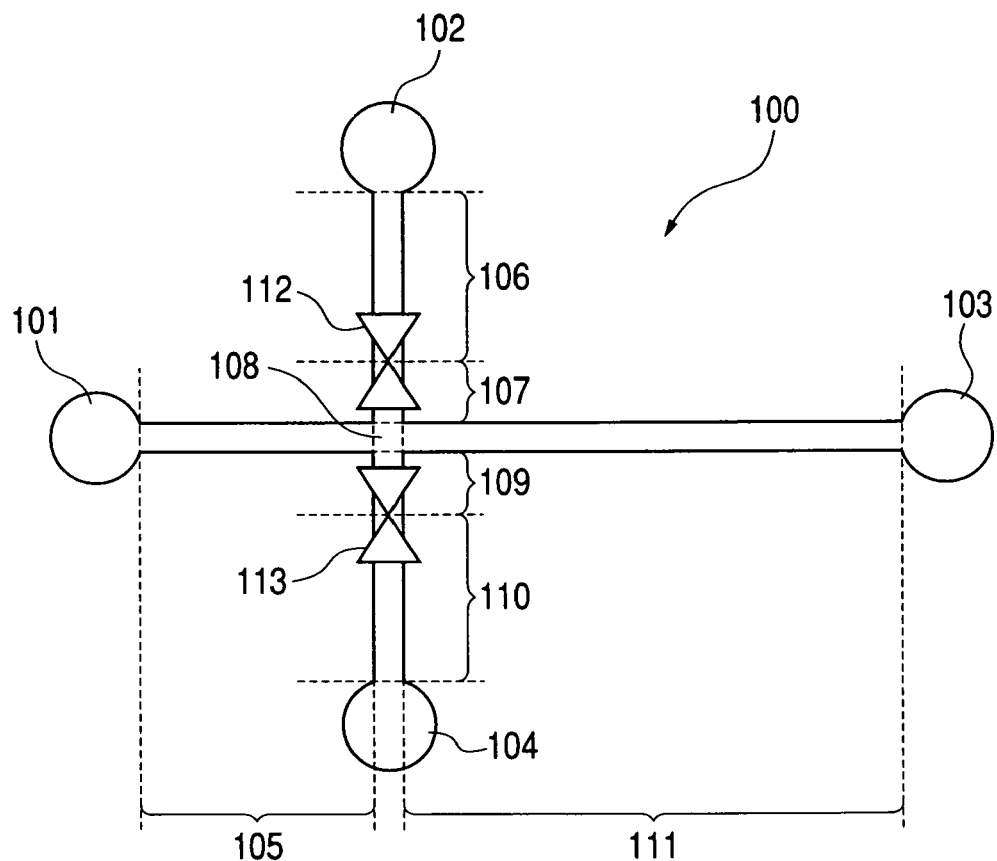
FIGS. 1A, 1B and 1C are schematic drawings showing an embodiment of a method of the present invention for introducing a liquid.
Figure 1B:
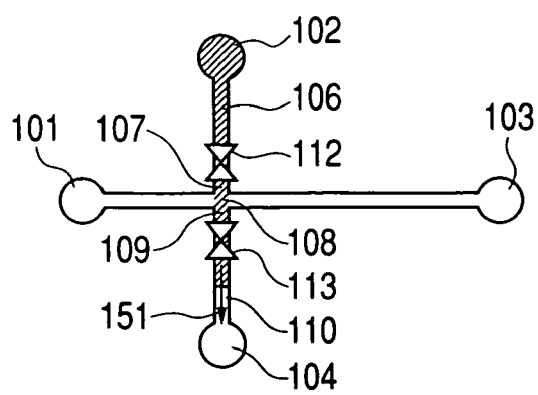
Figure 1C:
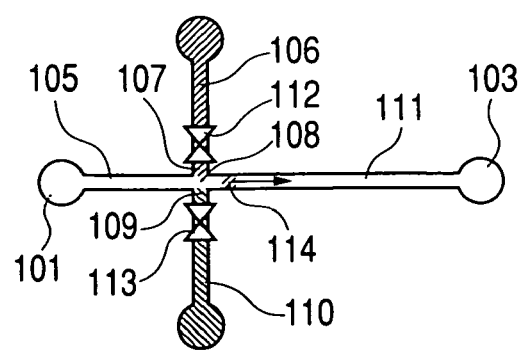

The fluid delivery device of the present invention is also applicable to a process for introducing a certain amount of a sample in a micro flow system. FIGS. 1A, 1B, and 1C show schematically an embodiment of the fluid delivery device of the present invention. The fluid delivery device 100 shown in FIG. 1A comprises flow channel 105 corresponding to a first flow channel, flow channel 106 and flow channel 107 corresponding to a second flow channel, flow channel 111 corresponding to a third flow channel, and flow channel 110 and flow channel 109 corresponding to a fourth flow channel, and injecting intersection 108 as an intersection portion of the four flow channels. Valve 112 corresponding to a first valve is provided between flow channel 106 and flow channel 107, and valve 113 corresponding to a second valve is provided between flow channel 109 and flow channel 110. Reservoir 101 is provided at the end of flow channel 105 at the side opposite to intersection 108, and reservoir 103 is provided at the end of flow channel 111 at the side opposite to intersection 108. Reservoir 102 is connected to the end of flow channel 106 at the side opposite to valve 112, and reservoir 104 is connected to the end of flow channel 110 at the side opposite to valve 113.

Reservoirs 101, 102, 103, 104 are respectively related to an electrode (not shown in the drawing). The electrodes are connected respectively through a control means for controlling the voltage of the respective electrodes to power sources (not shown in the drawing). To reservoir 101, a pump (not shown in the drawing) is connected to apply a pressure to the flow channel, and reservoir 103 is connected to an outside analysis apparatus. Valve 112 is a check valve which allows invariably a flow from channel 106 to flow channel 107 and intercepts a reverse flow. Valve 113 is designed to allow a flow from flow channel 109 to flow channel 110 at a pressure difference between the both faces of the valve lower than threshold $P_0$, and to intercept the flow at the pressure difference of not lower than $P_0$.

A process of cutting out a certain amount of a sample according to the present invention is explained regarding to liquid delivery device 100.

Step A:

In Step A, a first liquid is filled into the first flow channel, the second flow channel, the third flow channel, fourth flow channel and intersection portion of the four flow channels.

All of the flow channels and reservoirs in liquid delivery device 100 are made ready for use by filling a carrier liquid such as a buffer solution.

Step B:

In Step B, a second liquid is introduced into the second flow channel and the aforementioned intersection portion of the four flow channel, and the fourth flow channel in this order by use of a first liquid delivery mechanism.

Step B is explained by reference to FIG. 1B. A sample containing an analysis object material is introduced into reservoir 102. The potentials of the respective reservoir are adjusted to allow the sample to flow along a route from reservoir 102 through flow channel 106, valve 112, flow channel 107, injecting intersection 108, flow channel 109, valve 113, and flow channel 110 to reservoir 104. For instance, the potential at reservoir 102 is made higher than that at reservoir 104 to form the above flow. By bringing the potentials at reservoir 101 and reservoir 103 near to the potential at injecting intersection 108, ooze-out of sample from injecting intersection 108 to flow channel 105 or flow channel 111 is prevented. In this embodiment, since pressure difference $P_1$ caused in the valve is lower than pressure difference $P_0$, the threshold for valve closing, valve 113 is kept open in the step shown in FIG. 1B. Valve 112 is also kept open since the flow is directed from flow channel 106 to flow channel 107. In FIG. 1B, the hatched portion indicates the sample, and arrow 151 indicates the direction of sample flow.

Step C

In Step C, the second liquid near the cross-section of the aforementioned four flow channels is introduced into the third flow channel.

Step C is explained by reference to FIG. 1C. To reservoir 101, a pressure higher than that of the elecroosmotic flow is applied by a pump. Thereby, pressure difference $P_2$ in the valve becomes higher than threshold pressure difference $P_0$ to intercept the liquid flow from flow channel 109 to flow channel 110 at valve 113. Valve 112 also intercepts the liquid flow from flow channel 107 to flow channel 106. Thereby after application of the higher pressure, the flow of the liquid is limited to the route only from flow channel 105 through injecting intersection 108 to flow channel 111. This flow cuts out the fluid in injecting intersection 108 to form sample plug 114 and send it through flow channel 111 and reservoir 103 to an outside analysis apparatus.

Figure 2A:
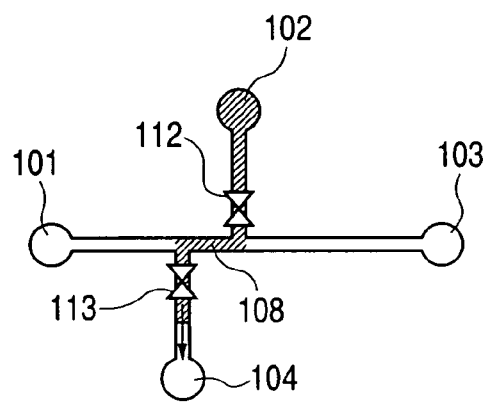
FIGS. 2A, 2B, 2C and 2D are schematic drawings showing another embodiment of a method of the present invention for introducing a liquid.
Figure 2B:
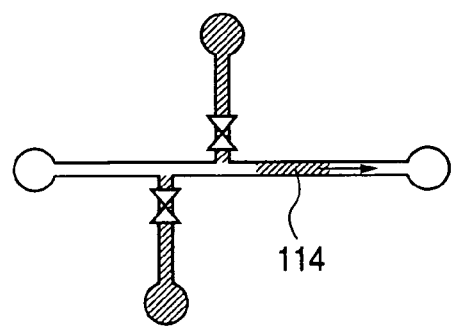
Figure 2C:
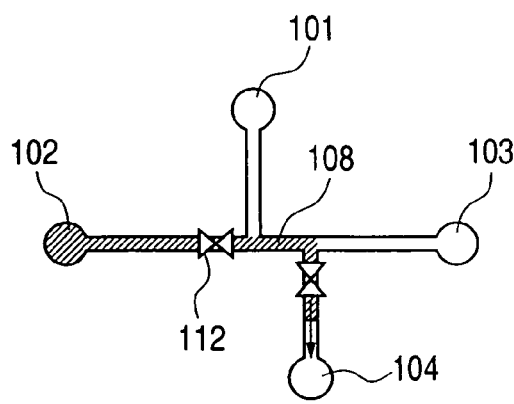
Figure 2D:
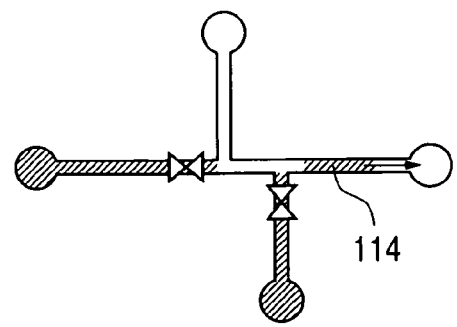

In another embodiment, as shown in FIGS. 2A and 2B, the second flow channel and the fourth flow channel are shifted laterally to adjust the length of the injection intersection portion 108 to change the amount of the sample plug. Further, as shown in FIGS. 2C and 2D, the first flow channel and the second flow channel may be exchanged in the position.

In Step C, valve 113 may be designed to allow a small amount of the fluid to flow from flow channel 109 to flow channel 110 without complete interception, which facilitates cut-out of the fluid in injecting intersection 108 to form stable sample plug 114.

In the above explanation, electroosmosis is employed as the first liquid delivery mechanism, and a pump is employed as the second liquid delivery mechanism. However, the liquid delivery mechanisms are not limited thereto. For example, pumps are employed as the first and second liquid delivery mechanisms, and a certain amount of the sample can be delivered by controlling the liquid delivery conditions. The pump may be controlled by controlling pressure and/or flow rate. A pipet may be employed as the liquid delivery mechanism.

The valve of the present invention is useful in various uses other than delivery of a certain amount of a sample. Various systems can be constructed by designing flow channel constitution, valve position, threshold pressures of the valve operation, liquid delivery conditions (pump delivery conditions, switching of electrodes for electroosmosis generation, etc.) in correspondence with an intended system.

(Fluid Delivery Device for Controlling Pressure-Generating Means for Liquid Delivery by Detection of Flow Rate)

Figure 10A:
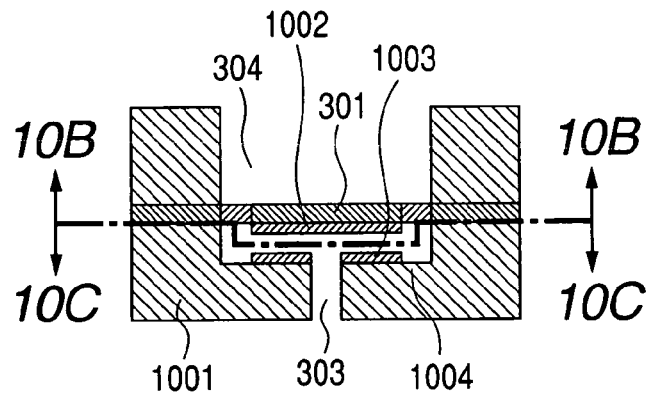
FIGS. 10A, 10B, 10C, 10D and 10E are schematic drawings showing an embodiment of a liquid delivery device of the present invention.
Figure 10B:
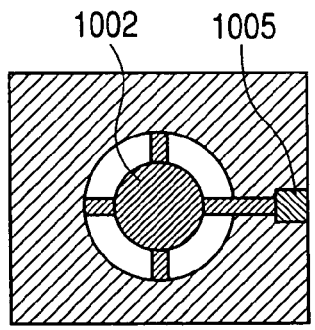
Figure 10C:
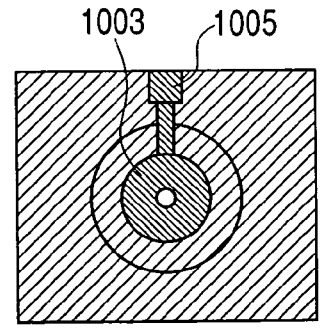

The fluid delivery device of the present invention is useful also for delivery of a fluid by controlling the flow rate. FIG. 10A shows an embodiment of the fluid delivery device of the present invention employed for control of a flow rate. FIG. 10B is a sectional view taken along line 10B-10B. FIG. 10C is a sectional view taken along line 10C-10C. In FIG. 10A, fluid delivery device 1001 has movable flat plate 301 which is operated by a pressure difference caused by a flow of a fluid between the upstream side and downstream side of the valve, first electrode (movable electrode) 1002 placed on the flat plate, valve sheet 1004, and second electrode (immovable electrode) 1003 placed on the valve sheet. Here, the "valve sheet" signifies the contact portion which comes to be in contact with flat plate 301 to intercept the channel 303 without the electrode. The first electrode and the second electrode may have respectively an insulating film thereon. A pump (not shown in the drawing) is connected to the upstream side of the fluid delivery device for delivering the fluid. First electrode 1002 and second electrode 1003 are connected (not shown in the drawing) to a detecting means for detecting the electrostatic capacity between the electrodes. The flow of the fluid is controlled by the electrostatic capacity detected by the detecting means.

The method for detecting the flow rate with the fluid delivery device of the present invention is explained below.

The electrostatic capacity produced between the first electrode and the second electrode is defined by the formula below:

$$C = \epsilon S/d \quad \text{[Formula 1]}$$

where C is the electrostatic capacity, $\epsilon$ is the dielectric constant of the fluid, S is the area of the electrode, and d is the distance between the electrodes.

Figure 10D:
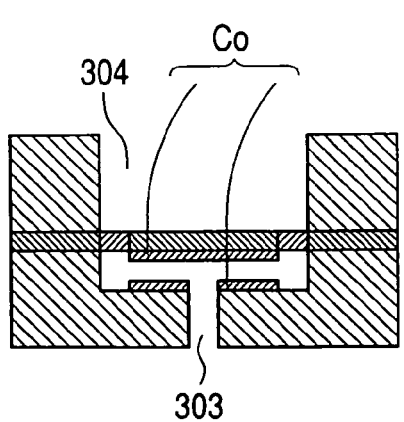
Figure 10E:
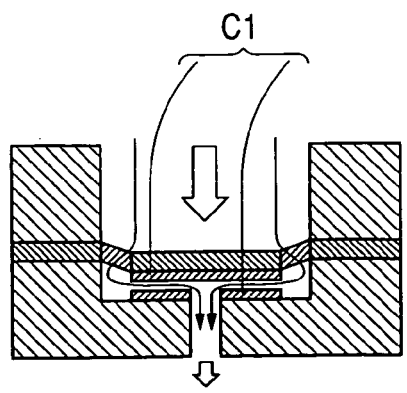

The electrostatic capacity at the initial state as shown in FIG. 10D is defined to be $C_0$ according to Formula 1. A flow of the fluid from channel 304 to channel 303 causes a pressure difference between the upstream side and the downstream side of flat plate 301 to move first electrode 1002 toward valve sheet 1004 as shown in FIG. 10E. Thereby, the distance between the electrode is shortened to change the electrostatic capacity from $C_0$ to $C_1$ ($C_1 > C_0$). The movement position of the flat plate depends on the flow rate. Therefore the flow rate can be calculated from measurement of the electrostatic capacity between the electrodes. Incidentally, in FIGS. 10B and 10C, the numeral 1005 denotes a lead-out wiring.

Figure 16:
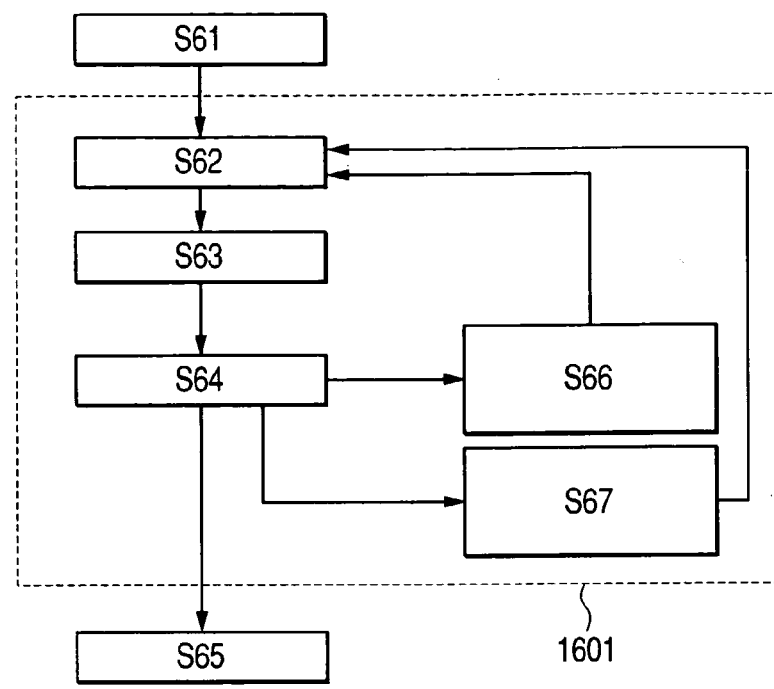
FIG. 16 is a flow chart of a process of controlling a fluid.

A process for controlling the flow rate by the fluid delivery device of the present invention is explained by reference to the flow chart in FIG. 16. In FIG. 16., the flow controlling process is surrounded by frame line 1601.

Firstly, a fluid is introduced (S61). Then the electrostatic capacity produced between the electrodes is measured (S62). The flow rate of the flow through the fluid delivery device of the present invention is derived from the measured electrostatic capacity (S63). Then judgment is made whether the derived flow rate is higher or lower than a predetermined reference flow rate (S64). When the flow rate is equal to the reference flow rate, the fluid is discharged outside (S65). When the flow rate is lower than the reference flow rate, command is given to the pump to increase the pressure (S66), whereas, when the flow rate is higher than the reference flow rate, command is given to the pump to lower the pressure (S67). By repeating the above steps, the fluid in the fine fluid system is controlled at an intended flow rate.

In the above example, a pump is used as the pressure generating means for delivery of the fluid, but is not limited thereto in the present invention. For instance, a heater is provided in the channel to heat the fluid and to deliver the fluid by utilizing the pressure of the gas, wherein the delivery flow rate can be controlled by controlling the heating conditions.

(Fluid Delivery Device for Controlling Pressure-Generating Means for Liquid Delivery in Accordance with Intended Flow Rate)

The fluid delivery device of the present invention is useful in delivery of a fluid by controlling a switch of external circuit for controlling the microchannel system in accordance with an intended delivery flow rate. In this case, the flow of the fluid is controlled by detecting the contact of first electrode (movable electrode) 1002 attached to flat plate 301 with second electrode (fixed electrode) 1003 attached to valve sheet 1004.

Figure 17:
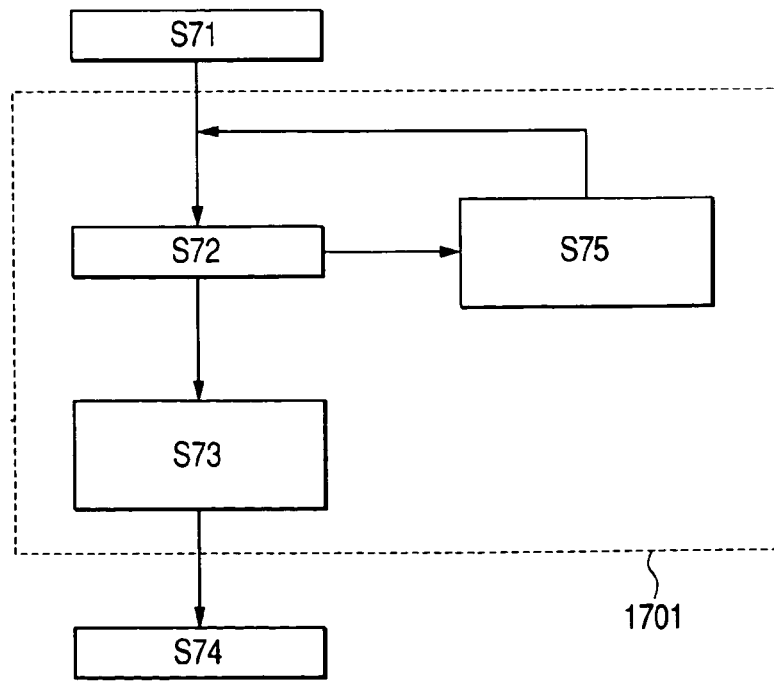
FIG. 17 is a flow chart of another process of controlling a fluid.

The process of controlling the flow rate in this embodiment is explained below by reference to FIGS. 11A, 11B, and 11C. FIG. 17 is a flow chart of this control process. In FIG. 17, the flow controlling process is surrounded by frame line 1701.

Figure 11A:
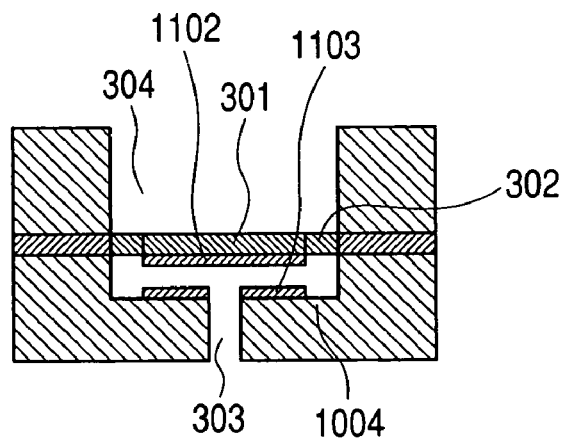
FIGS. 11A, 11B and 11C are schematic drawings showing a driving process of a fluid delivery device.
Figure 11B:
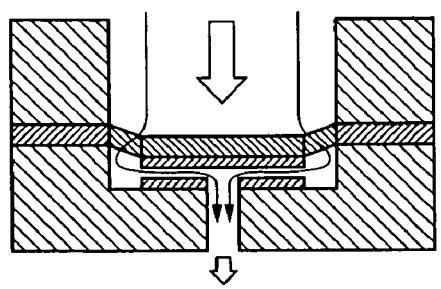
Figure 11C:
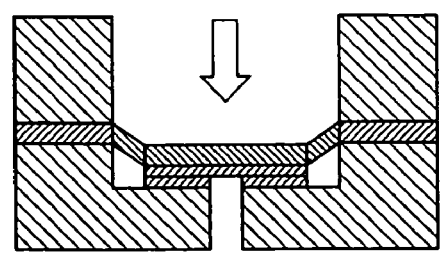

In the initial state in which the fluid is not flowing as shown in FIG. 11A, the electrodes keeps a predetermined distance and are not in contact with each other. With the flow of fluid from channel 304 to channel 303 (S71), a pressure difference is caused between the upstream side and downstream side of flat plate 301 to displace first electrode 1102 toward valve sheet 1004, and the fluid pressure difference is judged (S72). When the pressure difference caused by the fluid flow is less than the threshold pressure for closing the valve, the electrodes are not brought into contact as shown in FIG. 11B. With the electrode not in contact, a command is given to the pump to generate a pressure (S73), and the fluid is discharged outside (S74). When the pressure difference is larger than the threshold pressure for closing the valve, first electrode 1102 is bought into contact with second electrode 1103 as shown in FIG. 11C, and the contact is detected by an external circuit, and a command is given to the pump to stop generation of the pressure (S75), whereas when the pressure difference is smaller than the threshold pressure for closing the valve, the valve is opened by the righting moment of spring 302. In this open state in which first electrode 1102 and second electrode 1103 are not in contact, a command is given to the pump to generate a pressure. Thus the flow rate is controlled in the fine fluid system at an intended level by repeating the above steps. In FIGS. 11B and 11C, the blank arrow mark shows a relative flow rate of the fluid schematically.

In the above example, a pump is used as the pressure generating means for delivery of the fluid, but is not limited thereto in the present invention. For instance, a heater is provided in the channel to heat the fluid and to deliver the fluid by utilizing the pressure of the gas, wherein the delivery flow rate can be controlled by controlling the heating conditions.

Next, a device for controlling fuel feed in a fuel cell by use of the fluid delivery device of the present invention will be described. A fuel cell employing the fluid delivery device of the present invention is explained.

Figure 12A:
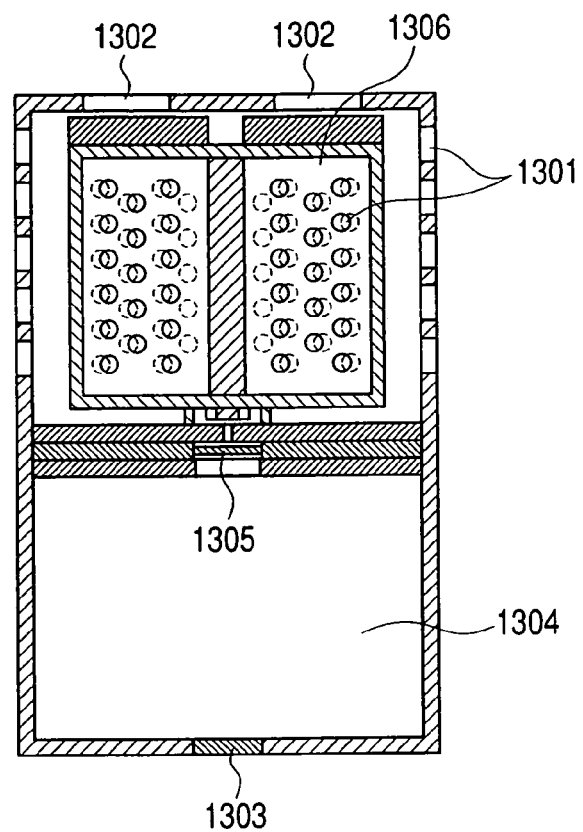
FIGS. 12A and 12B are schematic drawings showing a sectional structure of a fuel cell employing a fluid delivery device of the present invention.
Figure 12B:
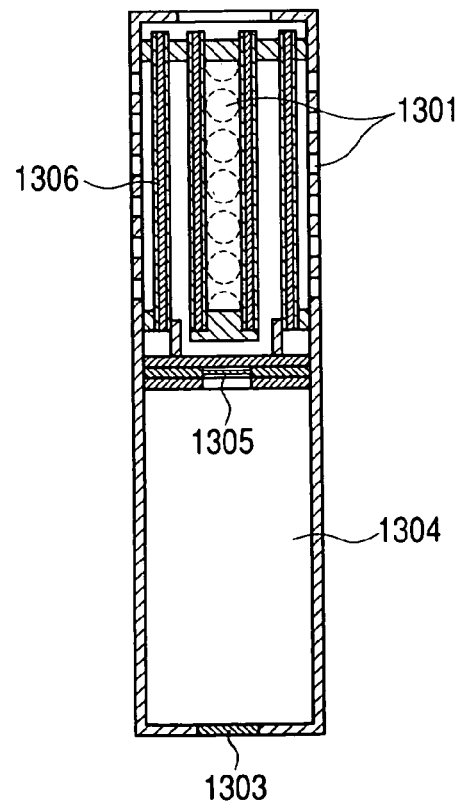
Figure 13:
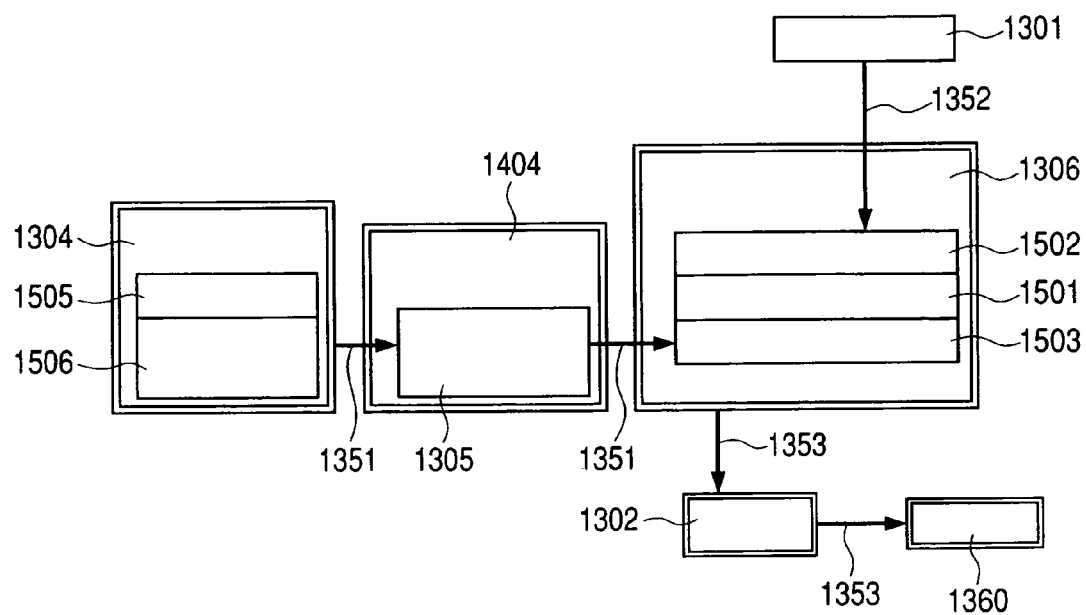
FIG. 13 is a block diagram showing a constitution of a fuel cell employing a fluid delivery device of the present invention.
Figure 14:
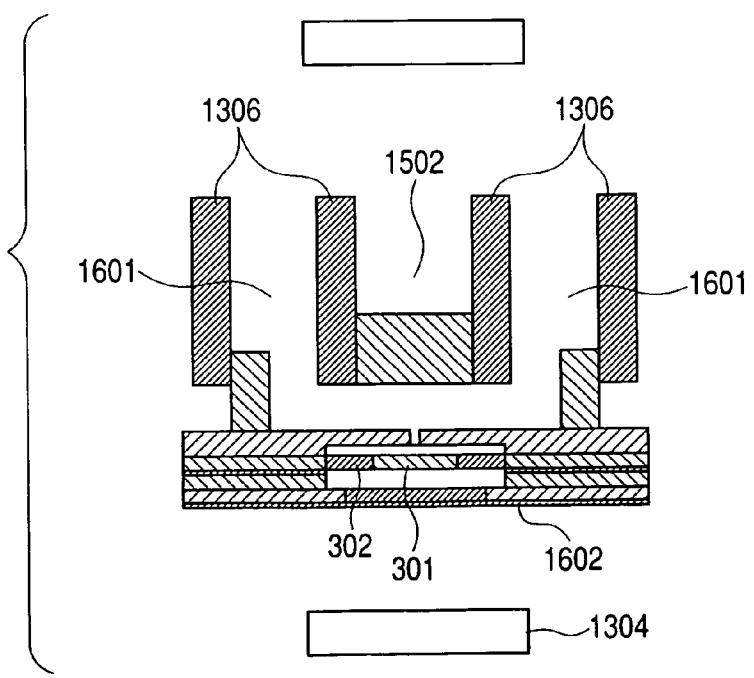
FIG. 14 is an enlarged drawing of a valve portion of a fuel cell of the present invention.

FIG. 12A is a plan view of the fuel cell. FIG. 12B is a front view of the fuel cell. FIG. 13 shows outline of the system of the fuel cell. FIG. 14 is an enlarged drawing of a microvalve shown in FIGS. 12A and 12B. The fuel cell has an external size of 50 mm×30 mm×10 mm, which is nearly the same size as the size of the lithium ion battery of an ordinary compact camera.

As shown in FIGS. 12A and 12B, the fuel cell has air holes 1301 on the upper face, the bottom face, and the side faces for taking in oxygen from outside air as an oxidant for the reaction. These air holes 1301 serve also to release formed water as water vapor and release the heat of the reaction to the outside. The fuel cell has also electrodes 1302 for taking out the electric power, and fuel charging hole 1303. As shown in FIG. 13, the fuel cell is constituted of polymer electrolyte film 1501, oxidizer electrode 1502 of the cell electrode, fuel electrode 1503, fuel battery cell (power generation section) 1306, fuel tank (fuel storage section) 1304, and fuel feeding section 1404 which connects the fuel tank and fuel electrodes of cells and has a valve for controlling the flow rate of the fuel. Further as shown in FIG. 14, the fuel feeding section is constituted of fuel electrode chamber 1601 for feeding the fuel to the fuel electrodes, oxidizer electrode chamber 1502 for feeding an oxidizer to the oxidizer electrode, and microvalve 1305 for controlling the fuel channel for fuel feed.

Fuel tank 1304 is filled a hydrogen-occluding metal which is capable of occluding hydrogen. The hydrogen-occuluding metal is exemplified by $LaNi_5$. The fuel tank occupies a half the volume of the entire fuel cell. The wall thickness of the tank is 1 mm. The construction material of the tank is titanium. The stored hydrogen is fed to the power generating cell by heating the hydrogen-occluding alloy.

The power generation process of the fuel cell is explained by reference to FIG. 13. The hydrogen is fed from fuel tank 1304 through fuel-supplying section 1404 to fuel electrode 1503. Arrow 1351 shows the hydrogen feed direction schematically. On the other hand, oxygen is fed from the outside through air hole 1301 to oxidizer electrode 1502. Arrow 1352 shows the air feed direction schematically. Thereby, electrochemical reaction occurs on the surface of polymer electrolyte film 1501 to generate electric power in the fuel cell. The generated electric power is supplied from electrode 1302 to a small electric appliance 1360. Arrow 1353 shows the supply direction of the generated electric power.

Figure 15A:
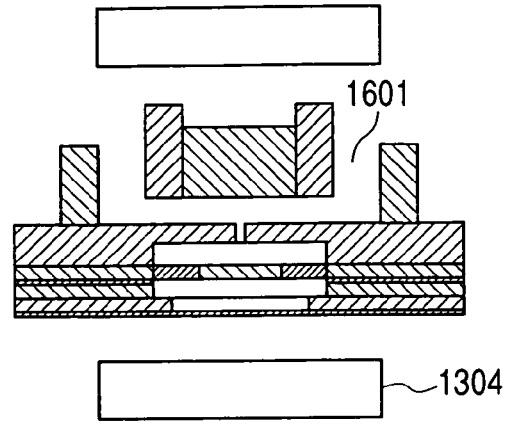
FIGS. 15A, 15B and 15C show control steps for controlling the flow rate in a fuel cell employing a fluid delivery device of the present invention.
Figure 15B:
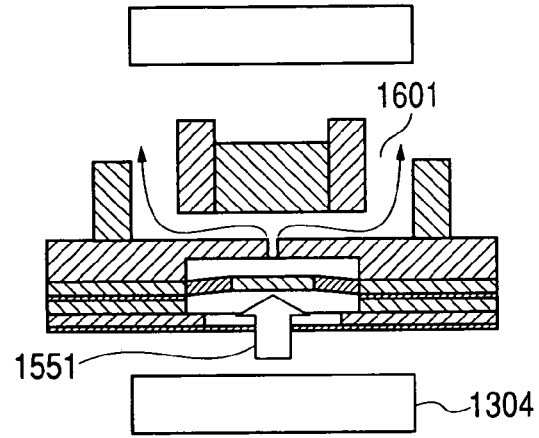

Next, the opening-closing operation of the valve for power generation of the fuel cell is explained by reference to FIGS. 15A, 15B, and 15C. During the shutdown, hydrogen is not fed from the fuel tank since the hydrogen in the fuel electrode chamber 1601 is not consumed. In this state, the valve is in an open state (FIG. 15A). On starting the power generation, the fuel in the fuel cell chamber is consumed, and the pressure of the fuel in the fuel electrode chamber decreases. Thus hydrogen is fed from the fuel tank through the valve, whereby the flat plate is moved toward the valve sheet side (FIG. 15B). On stopping the power generation, hydrogen consumption is stopped with the hydrogen remaining unconsumed in the fuel electrode chamber, and fuel feed comes to be stopped. Thereby, the flat plate comes to be in an open state (FIG. 15A).

Next, a function of the valve of the present invention as a stop valve for protecting the power generating cell is explained below.

(Function of Protection of Power-Generating Cell During Filling of Hydrogen to Fuel Tank)

For a sufficient amount of hydrogen occlusion in the fuel tank, the pressure in the fuel tank needs to be raised up to several atmospheres. On the other hand, the pressure at the power-generating cell side is about one atmosphere for utilizing the outside air. Therefore, an abrupt flow of the hydrogen from the fuel cell to the power-generating cell should be prevented for protection from damage of the interior of the power-generating cell.

The liquid delivery device of the present invention is provided between the fuel tank and the power-generating cell, whereby the valve of the present invention performs a function of preventing abrupt hydrogen inflow into the power-generating cell during hydrogen filling into the fuel tank.

Figure 15C:
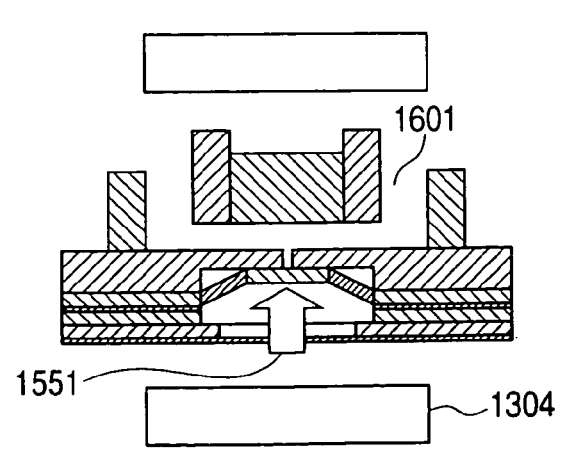

An excessive hydrogen inflow into the fuel feeding section closes the valve as shown in FIG. 15C to prevent abrupt inflow of the hydrogen into the power-generating cell and to protect the power-generating cell. The arrow 1551 shows the inflow of hydrogen from the fuel tank schematically.

The occlusion of hydrogen by the hydrogen occlusion alloy lowers the pressure in the fuel tank, decreasing the pressure difference between the fuel tank side and the power-generating cell side to be lower than the threshold pressure. Thereby the valve is opened by the righting moment of the spring, and the hydrogen comes to be fed to the power-generating cell (FIG. 15B).

As explained above, the fluid delivery device of the present invention serves as a stop valve for protecting the power-generating cell during filling of hydrogen to the fuel tank. The device begins fusel feed automatically with decrease of the pressure in the fuel tank.

(Function of Protecting Power-Generating Cell During Power Generation)

To a fuel cell, necessary hydrogen is fed by heating a hydrogen occlusion alloy by a heater. The interior of the power generating cell should be protected from damage by abrupt hydrogen supply to the power-generating cell by excessive temperature rise by malfunction of the heater.

The fluid delivery device of the present invention, which is placed between the fuel tank and the power-generating cell, performs a function of preventing abrupt inflow of hydrogen into the power-generating cell during power generation. When excessive hydrogen is introduced into the fuel feeding section by malfunction of the heater in the fuel tank, the valve of the present invention is capable of serving as a stop valve to stop the hydrogen feed.

Further, the fluid delivery device as shown in FIGS. 10A to 10E of the present invention, when used in the fuel cell, is capable of controlling the fuel flow by detecting the opening state of the valve. The control of the fuel flowing through the fluid delivery device can be conducted by detecting the electrostatic capacity between the electrodes. Therefore, the fluid delivery device of the present invention is effective in flow rate control in the fuel cell.

A fuel delivery control system can be realized by employing the fluid delivery device of the present invention.

The fuel control is conducted by detecting the electrostatic capacity at fixed time intervals to decrease the power consumption. Therefore, the present invention is useful especially for a miniature fuel cell in which the fuel is controlled precisely with a simple structure.

(Function for Detecting Operation State of Stop Valve)

During a hydrogen-filling operation, the valve should be closed for protection of the power-generating cell. The closed state of the valve can be detected by use of the fluid delivery device of the present invention. The normal functioning state of the stop valve can be detected by the fluid delivery device of the present invention. For instance, when the valve is not normally functioning owing to damage or other cause, the contact between the electrodes is not detected. In such a case, an alarm sound may be generated to inform the user about the disorder of the stop valve and danger of hydrogen leakage.

(Function of Detecting Completion of Hydrogen Filling Into Fuel Tank)

The fluid delivery device is useful for detecting the completion of hydrogen filling into the fuel tank. The hydrogen filled in the fuel tank is to be fed by opening the valve to the power-generating cell. The opening state of the valve can be detected by utilizing the switching function of the fluid delivery device of the present invention.

After completion of the hydrogen filling, the pressure in the fuel tank becomes lower. Thereby the pressure difference between the upstream side and downstream side of the valve decreases to be lower than the threshold pressure for valve closure. The decrease of the pressure difference results in opening of the valve to feed the hydrogen to the power-generating cell. The completion of the hydrogen filling can be known by detecting the detachment of the contacting electrodes.

The present invention is explained below in detail by reference to Examples. In Examples, dimensions, shapes, materials, and production process conditions mentioned are merely for illustration, and may be changed as design items within the range satisfying the requirement of the present invention.

EXAMPLE 1

In this Example, a liquid delivery device is practically produced which has valves controlled by pressure change of the fluid.

Figure 5A:
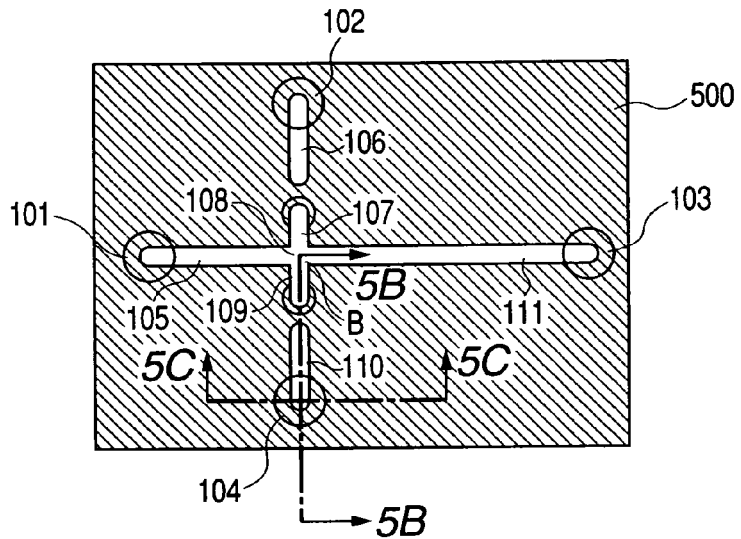
FIGS. 5A, 5B and 5C are schematic drawings showing still another embodiment of a liquid-controlling element driven by a pressure difference caused by flow of a liquid.
Figure 5B:
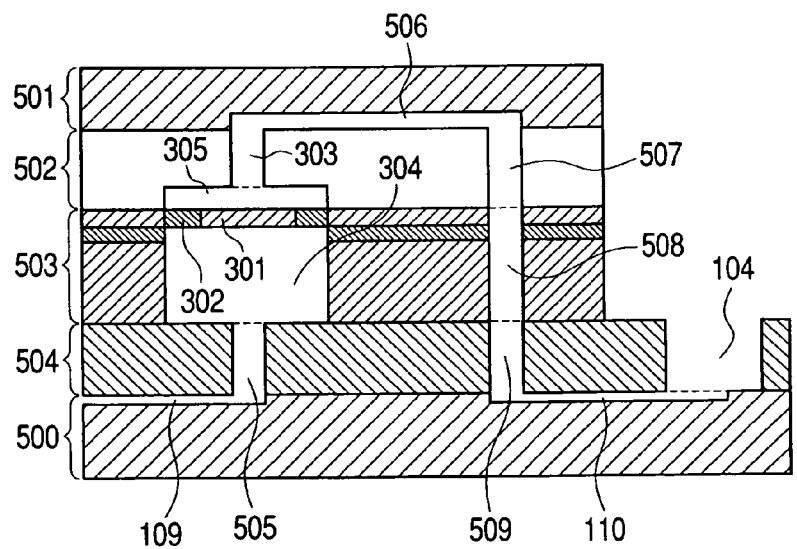
Figure 5C:
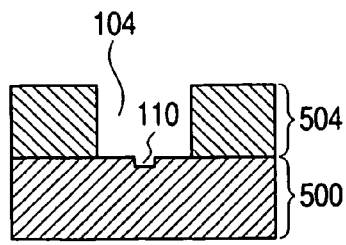

FIGS. 5A, 5B, and 5C show a specific example of production of the fluid delivery device shown in FIGS. 1A, 1B, and 1C. The fluid delivery device is constituted of substrates 500, 501, 502, 503, and 504 as shown in FIG. 5B. FIG. 5A is a plan view of substrate 500 in which channels shown in FIGS. 1A to 1C are formed. FIG. 5B is a sectional view taken along line 5B-5B in FIG. 5A. FIG. 5C is a plan view taken along line 5C-5C in FIG. 5A.

FIG. 5B shows specifically the route of fluid flow from flow channel 109 through the valve and flow channel 110 to reservoir 104. The fluid having passed through flow channel 109 in substrate 500 is injected via through-hole 505 in substrate 504 into large channel region 304 in substrate 503. Flat plate 301 provided in substrate 503 is displaced depending on the fluid pressure and the spring constant of spring 302. When the displaced flat plate 301 shuts the inlet of region 303 having a small channel in substrate 502, the fluid is stopped in large channel region 304 in substrate 502, not to flow into channel 303. On the other hand, when the displaced flat plate 301 does not shut the inlet to channel 303, the fluid passes through channels 305 and 303 to channel 506 in substrate 501, and thereafter the fluid passes via through hole 507 in substrate 502, through-hole 508 in substrate 503, and through-hole 509 in substrate 504 into flow channel 110 on substrate 500, and is discharged out of the system via reservoir 104.

The dimensions of parts of the device are exemplified below. Substrates 500, 501 have a thickness of 200 to 500 μm. Substrates 502, 504 have a thickness of 200 μm. The channels formed in substrates 500, 501 have a breadth of 100 μm and a depth of 20 to 100 μm. Substrate 503 is an SOI substrate having thicknesses silicon/silicon oxide film/silicon of 5 μm/0.5 μm/200 to 500 μm. Through-holes 303, 505, 507, 508, 509 formed on substrates 502, 503, 504 have diameter of 100 μm. Regions 304, 305 of a large channel have a diameter of 300 μm. The valve-forming flat plate 301 has a diameter of 200 μm, and a thickness of 5 μm. Spring 302 has a length of 50 μm, a thickness of 5 μm, and a breadth of 20 to 40 μm. The length of channel 305, namely the distance between non-displaced flat plate 301 and through-hole 303, is 5 μm. The respective reservoirs in substrate 504 have a diameter of 1 mm.

A process for producing the valve of this Example is explained below. FIGS. 6A to 6G illustrate the process for producing substrate 503, viewed at cross section corresponding to cross section B-B' in FIG. 5A.

Figure 6A:
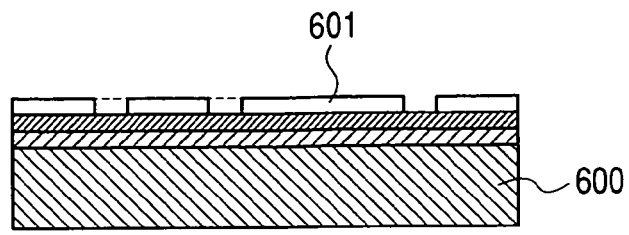
FIGS. 6A, 6B, 6C, 6D, 6E, 6F and 6G are flow sheets of production of a liquid-controlling element driven by a pressure difference caused by flow of a liquid.
Figure 6B:
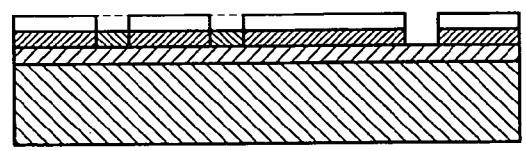

Firstly, on SOI substrate 600, on the side of 5 μm-thick silicon, a pattern of a valve comprising flat plate 301 and spring 302 shown FIG. 3A and through-hole 508 are formed by photolithography by use of photoresist 601 (FIG. 6A).

Next, SOI substrate 600 is dry-etched by $SF_6$-$C_4F_8$ gas plasma by use of photoresist 601 as the etching mask to form flat plate 301 of depth of 5 μm, spring 302, and a part of through-hole 508 (FIG. 6B) by utilizing the silicon oxide layer as the etching stopper.

Figure 6C:
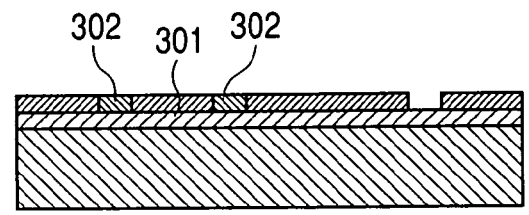

Thereafter, the photoresist is removed by $O_2$ plasma treatment. The substrate is washed by a mixture of a sulfuric acid solution and an aqueous hydrogen peroxide solution at a temperature of 110° C. (FIG. 6C).

Figure 6D:
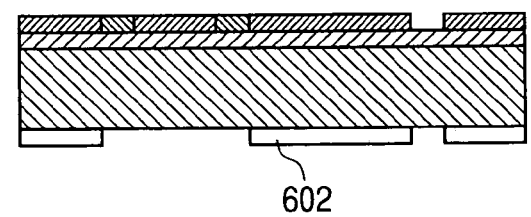

On SOI substrate 600 on the side of the silicon of thickness of 200 to 500 μm, a pattern of a part of channel 304 and a part of through-hole 508 by photolithography by using photoresist 602 (FIG. 6D).

Figure 6E:
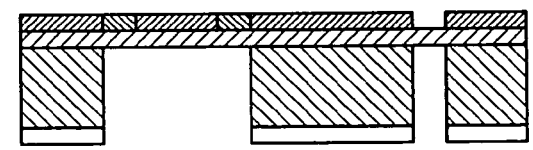

SOI substrate 600 is dry-etched by $SF_6$—$C_4F_8$ gas plasma by use of photoresist 602 as the etching mask to reach and bare the silicon oxide film as the etching stopper to form a part of channel 304 and a part of through-hole 508 (FIG. 6E).

Figure 6F:
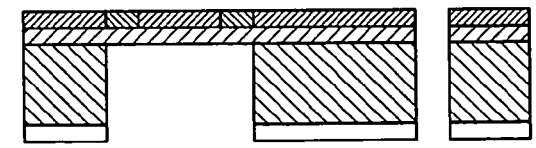

The bared portion of the silicon oxide film of SOI substrate 600 is dry-etched by a CF type gas plasma by using photoresist 602 as the etching mask to form channel 304 and through-hole 508 (FIG. 6F).

Figure 6G:
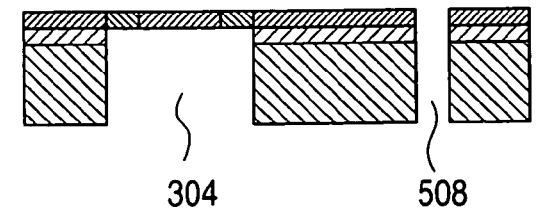

Finally, the photoresist is removed by $O_2$-plasma treatment, and the substrate is washed with a mixture solution of sulfuric acid and aqueous hydrogen peroxide at 110° C. (FIG. 6G).

The structure of substrate 503 is finished through the above steps.

As substrates 500 and 501, glass plates are patterned to form channels by photolithography and wet etching by HF. As substrate 502, silicon is used, and the silicon is treated by combination of photolithography and $SF_6$—$C_4F_8$ gas plasma dry-etching in a similar manner as substrate 503. As substrate 504, glass is used, and the glass is sand-blasted to form through-holes.

Substrates 500, 501, 502, 503, and 504 are bonded by thermal fusion (not shown in the drawing).

EXAMPLE 2

Figure 7A:
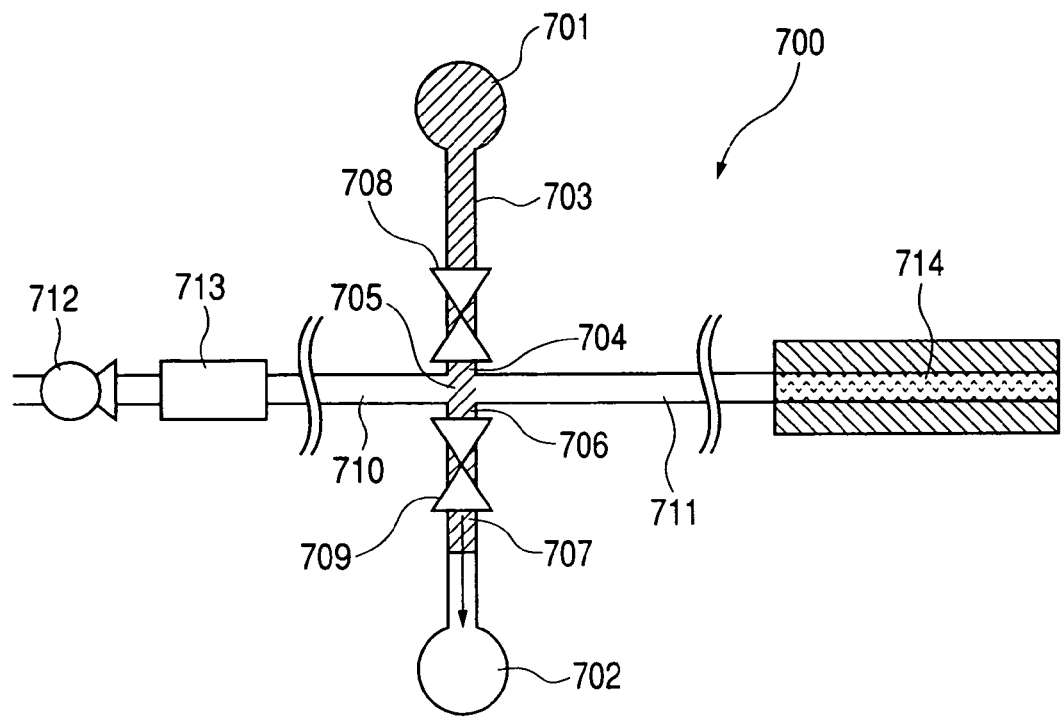
FIGS. 7A and 7B are schematic drawings showing an example of a method of the present invention for introducing a liquid.
Figure 7B:
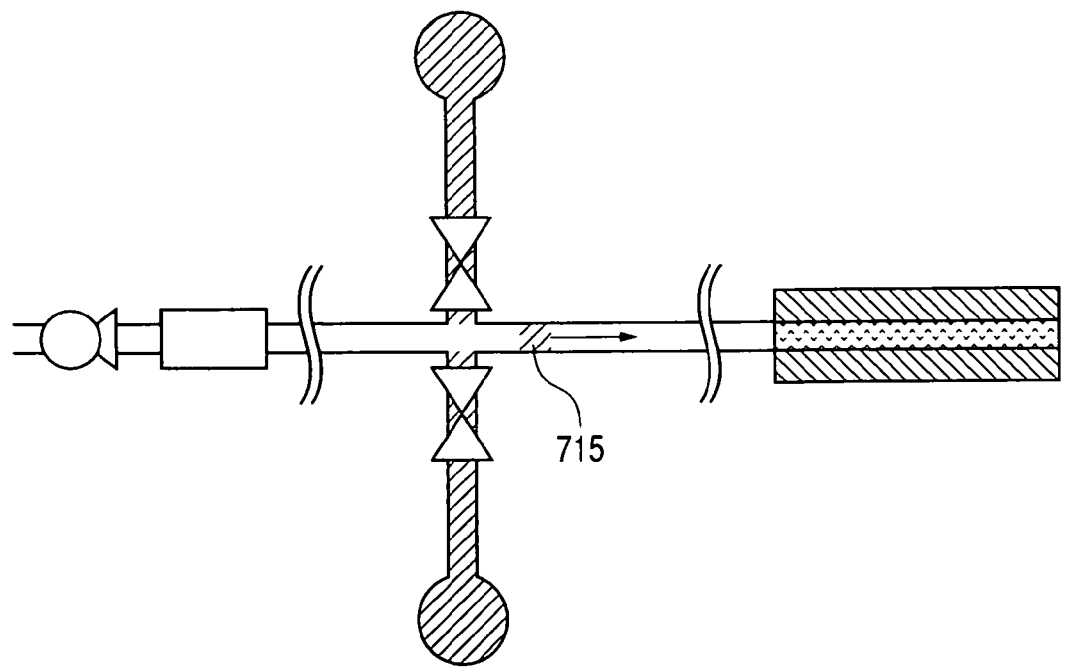
Figure 8A:
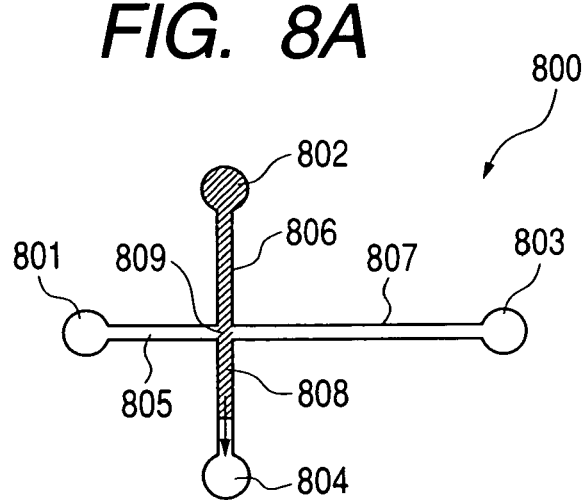
FIGS. 8A, 8B and 8C are schematic drawings showing a conventional method for introducing a liquid.
Figure 8B:
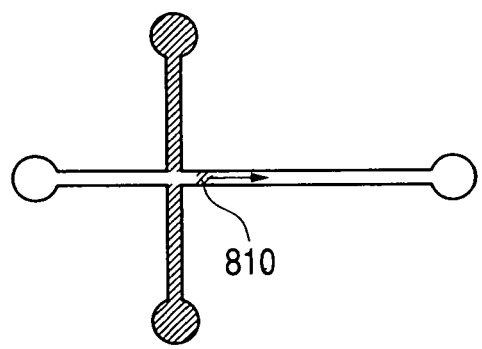
Figure 8C:
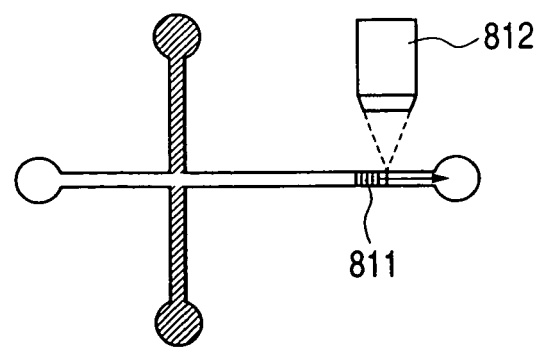

With the device prepared above as shown in FIGS. 5A, 5B, and 5C, a unit for separation and analysis is constructed for analysis of a mixture solution containing benzoic acid, salicylic acid, and phenol by HPLC (high performance liquid chromatography). FIGS. 7A and 7B illustrate the unit schematically.

Unit 700 is constructed on a substrate, having first channel 710, second channel 703-704, third channel 711, fourth channel 706-707, injecting intersection 705, valve 708 in channel 703-704, and valve 709 in channel 706-707. Reservoir 701 is connected to the end of flow channel 703 at the side opposite to valve 708, and reservoir 702 is connected to the end of flow channel 707 at the side opposite to valve 709. Flow channel 710 is connected to pump 712 and flow controller 713 at the outside of unit 700 at the channel end opposite to intersection 705 for injection. Flow channel 711 is connected to an outside analysis apparatus, HPLC column 714, at the channel end opposite to injecting intersection 705.

Valves 708 and 709 are respectively a liquid differential-pressure driven type of valve shown FIG. 5B. Flow channels 109 and 110 in FIG. 5B correspond respectively to flow channels 704 and 703 of valve 708, and to flow channels 706 and 707 of valve 709. An electrode is connected (not shown in the drawing) to each of reservoirs 701 and 702 to control movement of the fluid by electroosmosis.

The analysis object sample solution is an aqueous mixture solution of benzoic acid, salicylic acid, and phenol in 100-mM phosphate buffer solution (pH=7.0; $KH_2PO_4$—$Na_2HPO_4$). The mobile phase solution is a mixture of the above phosphate buffer solution and methanol (mixing ratio 75:25).

The process of analysis is shown below. Firstly, the inside of the flow channel in the unit 700 is entirely filled with the mobile phase solution (not shown in the drawing). An analysis object sample solution is introduced from reservoir 701, and is delivered, as shown in FIG. 7A, by electroosmosis through flow channel 703, valve 708, flow channel 704, injecting intersection 705, flow channel 706, valve 709, and flow channel 707 to reservoir 702. For the delivery, the potential of reservoir 701 is set at 5 kV, and reservoir 702 is grounded. In the step of FIG. 7A, valve 708 and valve 709 are kept open.

Then as shown in FIG. 7B, a pressure exceeding the electroosmotic flow is applied to flow channel 710 by pump 712. This applied pressure closes valve 708 and valve 709, and cuts out the solution in the portion of injecting intersection 705 as sample plug 715 to move it by the pressed flow through flow channel 711 and introduces it into HPLC column 714 of an outside analysis apparatus. The pressure applied by the pump is 0.1 to 0.3 MPa.

This HPLC column 714 is a reversed phase chromatographic column employing an ODS (octadecylated silica). The separated components are detected respectively by a UV absorption detector at a UV wavelength of 280 nm. As the result, three distinct output signal peaks are obtained according to the elution times of benzoic acid, salicylic acid, and phenol.

As described above, a system can be constructed which cuts out an intended amount of a sample and delivers it by a pressed stream by combination of an electroosmotic flow and a pressure driven flow to control the flow of a solution. In particular, the present invention is useful in HPLC which requires high pressure much higher than electroosmotic pressure for sample injection.

EXAMPLE 3

With the device for analysis of FIGS. 5A, 5B, and 5C, an HPLC apparatus is constructed for separation and analysis of five kinds of proteins in a solution including glutamate dehydrogenase, lactate dehydrogenase, enolase, adenylate kinase, and cytochrome c. FIGS. 7A and 7B show the device schematically.

Unit 700 is constructed on a substrate, having first channel 710, second channel 703-704, third channel 711, fourth channel 706-707, injecting intersection 705, valve 708 in channel 703-704, valve 709 in channel 706-707. Reservoir 701 is connected to the end of flow channel 703 at the side opposite to valve 708, and reservoir 702 is connected to the end of flow channel 707 at the side opposite to valve 709. Flow channel 710 is connected to pump 712 and flow controller 713 at the outside of unit 700 at the channel end opposite to intersection 705 for injection. Flow channel 711 is connected to an outside analysis apparatus, HPLC column 714, at the channel end opposite to injecting intersection 705.

Valves 708 and 709 are respectively a liquid differential-pressure driven type of valve shown FIG. 5B. Flow channels 109 and 110 in FIG. 5B correspond respectively to flow channels 704 and 703 of valve 708, and to flow channels 706 and 707 of valve 709. An electrode is connected (not shown in the drawing) to each of reservoirs 701 and 702 to control movement of the fluid by electroosmosis.

The analysis object sample solution is an aqueous mixture solution containing the aforementioned five proteins in a 50 mM phosphate buffer solution (pH=7.0) containing 0.3M NaCl (final concentration of each protein being 1.5 mg/mL). The mobile phase solution is a mixture of the above phosphate buffer solution and methanol (mixing ratio 75:25).

The process of analysis is shown below. Firstly, the inside of the flow channel in the unit 700 is entirely filled with the mobile phase solution (not shown in the drawing). An analysis object sample solution is introduced from reservoir 701, and is delivered, as shown in FIG. 7A, by electroosmosis through flow channel 703, valve 708, flow channel 704, injecting intersection 705, flow channel 706, valve 709, and flow channel 707 to reservoir 702. For the delivery, the potential of reservoir 701 is set at 5 kV, and reservoir 702 is grounded. In the step of FIG. 7A, valve 708 and valve 709 are kept open.

Then as shown in FIG. 7B, a pressure exceeding the electroosmotic flow is applied to flow channel 710 by pump 712. This applied pressure closes valve 708 and valve 709, and cuts out the solution at the portion of injecting intersection 705 as sample plug 715 to move it by the pressed flow through flow channel 711 and introduces it into HPLC column 714 of an outside analysis apparatus. The pressure applied by the pump is 0.1 to 0.3 MPa.

This HPLC column 714 is of a silica type GFC (size separation) mode. The separated proteins are detected respectively by a UV absorption detector at a UV wavelength of 280 nm. As the result, five distinct output signal peaks of glutamate dehydrogenase, lactate dehydrogenase, enolase, adenylate kinase, and cytochrome c are obtained according to the elution times relating to the molecular weights.

As described above, a system can be constructed which cuts out an intended amount of a sample and delivers it by a pressed stream by combination of an electroosmotic flow and a pressed flow to control the flow of a solution. In particular, the present invention is useful in HPLC which requires high pressure much higher than electroosmotic pressure for sample injection.

EXAMPLE 4

In this Example, a flow rate of a fluid is controlled according to an electrostatic capacity with the fluid delivery device shown in FIGS. 10A to 10E.

The fluid delivery device in FIGS. 10A to 10E.

Figure 18:
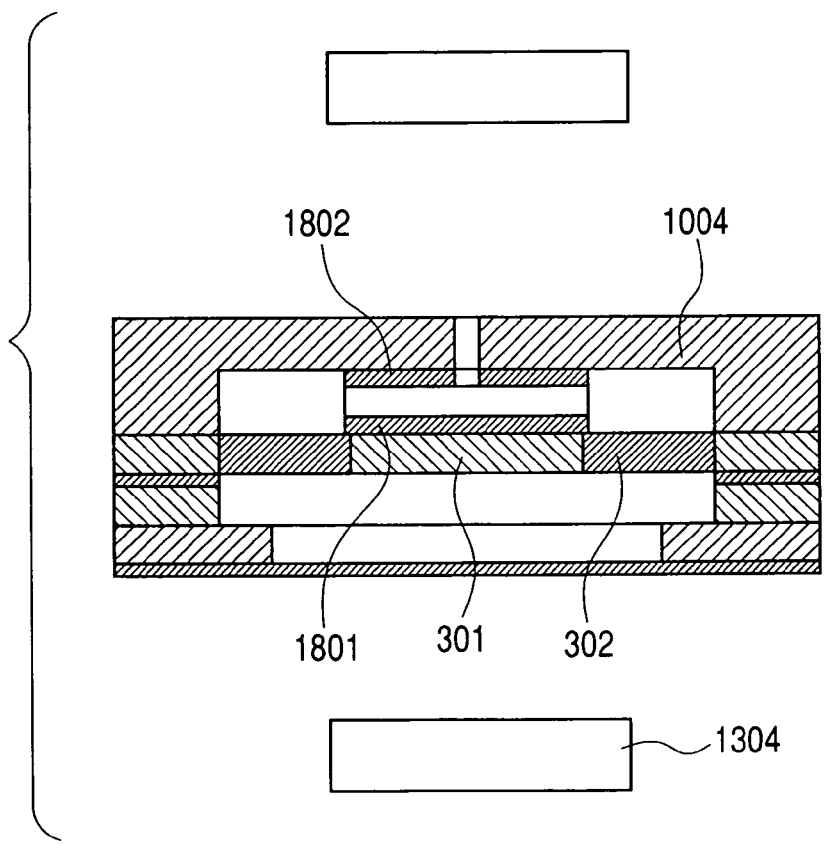
FIG. 18 is a schematic drawing of an embodiment of a fuel cell employing a liquid delivery device of the present invention.

The fluid delivery device in FIGS. 10A to 10E is employed in a fuel cell mounted on a digital camera. The fluid delivery device is placed in the channel between a fuel storing section and a power generating section. FIG. 18 is an enlarged drawing of the valve connected to the fuel cell. In the fluid delivery device of FIG. 18, first electrode 1801 is provided on flat plate 301, and second electrode 1802 is provided on valve sheet 1004. An insulating film (not shown in the drawing) may be provided on the first electrode and/or the second electrode. An external circuit (not shown in the drawing) is connected to the first electrode and the second electrode for detecting the electrostatic capacity between the electrodes. The material for the electrodes is aluminum. The material for the insulating film is a silicon oxide film. The hydrogen occlusion alloy in the fuel tank is $LaNi_5$. The digital camera consumes an electric power of 7 W. For producing this power, the hydrogen is fed at a flow rate of 50 mL/min. Therefore, in this device, the normal feeding rate is set at 50 mL/min.

The process of delivering the fuel by controlling the fuel flow rate is explained below.

On receiving a command for power generation, the fuel is delivered from the fuel tank to the fuel electrode. In this step, the hydrogen flow rate is found to be 20 mL/min by electrostatic capacity measurement being lower than the normal flow rate of 50 mL/min. Therefore, heating of $LaNi_5$ is started. The heating increases the hydrogen dissociation pressure of $LaNi_5$ to increase the hydrogen delivery pressure. The hydrogen flow rate is found to be 70 mL/min by electrostatic capacity measurement. Since the measured flow rate is higher than the normal flow rate, $LaNi_5$ is cooled to lower the hydrogen dissociation pressure of $LaNi_5$ to lower the hydrogen delivery pressure. Thereby, the delivery rate of the hydrogen is found to be 50 mL/min according to electrostatic capacity measurement.

By repeating the above steps, the normal flow rate of 50 mL/min can be maintained precisely. As the result, the fuel cell generates the power of 7 W, enabling stable use of the digital camera.

As described above, the flow rate of the hydrogen through the valve can be controlled at a prescribed level by controlling the hydrogen producing pressure according to the hydrogen flow rate measurement. In particular, in miniature fuel cells, the fuel should be precisely fed with a simple structure. This Example shows the effectiveness of the present invention.

EXAMPLE 5

In this Example, the feed of a fuel is controlled by detecting an opening state of a valve with the fluid delivery device shown in FIGS. 10A to 10E.

The fluid delivery device in FIGS. 10A to 10E is employed in a fuel cell mounted on a digital camera. The fluid delivery device is placed in the channel between a fuel storing section and a power generating section. FIG. 18 is an enlarged drawing of the valve connected to the fuel cell. In the fluid delivery device of FIG. 18, first electrode 1801 is provided on flat plate 301, and second electrode 1802 is provided on valve sheet 1004. An external circuit (not shown in the drawing) is connected to the first electrode and the second electrode for detecting the contact between the electrodes. The material for the electrodes is aluminum. The hydrogen occlusion alloy in the fuel tank is $LaNi_5$. The small electronic unit consumes an electric power of 7 W. For producing this power, the hydrogen is fed at a flow rate of 50 mL/min. The valve is designed to close when the hydrogen flow rate reaches 100 mL/min.

The process of delivering the fuel by controlling the opening of the valve by detecting the opening state of the valve is explained below.

On receiving a command for power generation, hydrogen is delivered from the fuel tank to the fuel electrode. The flow of hydrogen through the valve displaces flat plate 301 toward valve sheet 1004. After detection of the opening state of the valve, heating of $LaNi_5$ is started. Thereby the hydrogen dissociation pressure of $LaNi_5$ increases to increase the hydrogen delivery pressure. Next, assuming occurrence of malfunction of the heater, the fuel storage section is forcibly heated from outside. Thereby the hydrogen dissociation pressure rises to increase the hydrogen delivery pressure. This increases the hydrogen flow rate in the valve to 100 mL/min or more, and closes the valve. The resulting contact between the electrodes is detected by the external circuit, which stops the heating of $LaNi_5$. As the results, the hydrogen dissociation pressure becomes lower; hydrogen delivery pressure is lowered; the pressure difference between the fuel storage section side and the power generation section side of the valve is made lower than the threshold pressure of valve closing, and the valve is opened by righting moment of spring 302. By repeating the above steps, the hydrogen flow through the valve can be controlled.

As described above, the hydrogen delivery can be controlled by detecting the valve opening state, and repeating heating of $LaNi_5$ according to the valve opening state. In such a manner, the power generation section is protected from damage by abrupt rise of, hydrogen generation pressure by malfunction of the heater, and the activation of the heater can be stopped until the hydrogen generation pressure decreases to the prescribed pressure. In particular, in miniature fuel cells, the fuel should be precisely fed with a simple structure. This Example shows the effectiveness of the present invention.

The invention claimed is:

1. A fluid delivery device comprising:
   a flow channel formed on a substrate; and
   valves for controlling a flow of a fluid in the flow channel,
   wherein the flow channel comprises a first flow channel, a second flow channel branched from the first flow channel, a third flow channel connected to the first flow channel, and a fourth flow channel in communicating with the second flow channel by way of the first flow channel, and
   a first valve formed in the second flow channel being a check valve that allows invariably a flow toward the first flow channel and intercepts a flow in a reverse direction, or a threshold valve that allows invariably a flow toward the first flow channel, and in the reverse direction operates in accordance with a pressure difference between an upstream side and a downstream side of the first valve caused by the flow of the fluid, allowing the fluid to flow when the pressure difference is lower than a prescribed value $P_0$, and intercepting the fluid not to flow when the pressure difference is $P_0$ or more, a second valve formed in the fourth flow channel being a threshold valve, and the first valve and the second valve each having a layer and controlling the flow of the fluid in the second and fourth flow channels by elastically deforming the layer on the substrate, and wherein the fluid introduced from the second flow channel toward the fourth flow channel and located in the first flow channel and also between the first valve and the second valve is delivered toward the third flow channel.

2. The fluid delivery device according to claim 1, wherein further comprising a fluid element for analysis of the fluid connected to the third flow channel.

3. The fluid delivery device according to claim 2, wherein resistance to the flow in the third flow channel is higher than resistance to the flow in the second flow channel when the first valve is open.

4. The fluid delivery device according to claim 3, wherein the fluid element is a column of liquid chromatography.

5. The fluid delivery device according to claim 4, wherein the column of liquid chromatography is provided for analysis of a chemical substance contained in the fluid.

6. The fluid delivery device according to claim 4, wherein the column of liquid chromatography is a column for analysis of a protein contained in the fluid.

7. The fluid delivery device according to claim 1, wherein the layer is formed in a large flow channel apart from a small flow channel, and the layer intercepts the flow into the small flow channel by being deformed elastically.

* * * * *